United States Patent
Zhong et al.

(10) Patent No.: US 12,116,331 B2
(45) Date of Patent: Oct. 15, 2024

(54) GAS REPLACEMENT PROCESS, GAS REPLACEMENT APPARATUS, AND NITRO COMPOUND HYDROGENATION REACTION PROCESS

(71) Applicants: CHINA PETROLEUM & CHEMICAL CORPORATION, Beijing (CN); SHANGHAI RESEARCH INSTITUTE OF PETROCHEMICAL TECHNOLOGY SINOPEC, Shanghai (CN)

(72) Inventors: Siqing Zhong, Shanghai (CN); Jun Xu, Shanghai (CN); Le Zhao, Shanghai (CN); Lianghua Wu, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

( * ) Notice: Subject to any disclaimer, the term of this patent is extended or adjusted under 35 U.S.C. 154(b) by 752 days.

(21) Appl. No.: 17/286,576

(22) PCT Filed: Oct. 17, 2019

(86) PCT No.: PCT/CN2019/111638
§ 371 (c)(1),
(2) Date: Apr. 19, 2021

(87) PCT Pub. No.: WO2020/078411
PCT Pub. Date: Apr. 23, 2020

(65) Prior Publication Data
US 2021/0387153 A1 Dec. 16, 2021

(30) Foreign Application Priority Data
Oct. 17, 2018 (CN) .......................... 201811207014.5

(51) Int. Cl.
*B01J 8/18* (2006.01)
*B01J 8/00* (2006.01)
(Continued)

(52) U.S. Cl.
CPC .......... *C07C 209/36* (2013.01); *B01J 8/0055* (2013.01); *B01J 8/1809* (2013.01); *B01J 8/1827* (2013.01);
(Continued)

(58) Field of Classification Search
CPC ................. C07C 209/36; C07C 211/46; C07C 2523/72; B01J 8/0055; B01J 8/1809;
(Continued)

(56) References Cited

U.S. PATENT DOCUMENTS

| | | | |
|---|---|---|---|
| 5,380,426 A | 1/1995 | Johnson et al. | |
| 6,652,736 B1 | 11/2003 | Barthod et al. | |
| 9,533,939 B2 | 1/2017 | Mitchell et al. | |

FOREIGN PATENT DOCUMENTS

| | | | |
|---|---|---|---|
| CN | 1270853 A | | 10/2000 |
| CN | 1335356 A | * | 2/2002 |

(Continued)

OTHER PUBLICATIONS

Jiang, Xinliang; "Application of Cu—SiO2 catalyst in aminobenzene production"; Chlor-Alkali Industry; vol. 45, No. 9; Sep. 2009; pp. 30-34.

*Primary Examiner* — Huy Tram Nguyen
(74) *Attorney, Agent, or Firm* — NKL Law; Allen Xue

(57) ABSTRACT

A gas replacement process and a gas replacement apparatus are employed, in the nitro compound hydrogenation reaction process. The gas replacement process at least includes a first step of subjecting a stream to be replaced to the gas replacement in presence of a first replacement gas, and then a second step of subjecting to the gas replacement in (Continued)

presence of the second replacement gas. Assuming the superficial velocity of the first replacement gas is V1, and the superficial velocity of the second replacement gas is V2, then $V2/V1 \geq 1.5$.

15 Claims, 3 Drawing Sheets

(51) Int. Cl.
*B01J 8/24* (2006.01)
*B01J 21/08* (2006.01)
*B01J 23/72* (2006.01)
*B01J 23/94* (2006.01)
*B01J 35/40* (2024.01)
*B01J 38/06* (2006.01)
*C07C 209/36* (2006.01)

(52) U.S. Cl.
CPC ............... *B01J 8/24* (2013.01); *B01J 21/08* (2013.01); *B01J 23/72* (2013.01); *B01J 23/94* (2013.01); *B01J 35/40* (2024.01); *B01J 38/06* (2013.01); *B01J 2208/00752* (2013.01)

(58) Field of Classification Search
CPC ............ B01J 8/1827; B01J 8/24; B01J 21/08; B01J 23/72; B01J 23/94; B01J 35/40; B01J 38/06; B01J 2208/00752; B01J 2219/30211; B01J 2219/30253; B01J 2208/00132; B01J 2219/30226; B01J 2219/30238; B01J 8/1836; B01J 8/1863; B01J 8/34; B01J 8/44; B01J 38/04; B01J 8/18; Y02P 20/584
USPC ........................................................ 422/144
See application file for complete search history.

(56) References Cited

FOREIGN PATENT DOCUMENTS

| | | | | |
|---|---|---|---|---|
| CN | 1528737 | A | | 9/2004 |
| CN | 1634860 | A | | 7/2005 |
| CN | 2757912 | Y | | 2/2006 |
| CN | 1754625 | A | * | 4/2006 |
| CN | 1762567 | A | | 4/2006 |
| CN | 101016247 | A | | 8/2007 |
| CN | 101474582 | A | | 7/2009 |
| CN | 102443419 | B | * | 7/2014 |
| CN | 106732822 | A | | 5/2017 |
| JP | 2010260858 | A | | 11/2010 |
| RU | 2398813 | C2 | | 1/2010 |
| RU | 2597084 | C2 | | 9/2016 |

* cited by examiner

GAS REPLACEMENT PROCESS, GAS REPLACEMENT APPARATUS, AND NITRO COMPOUND HYDROGENATION REACTION PROCESS

TECHNICAL FIELD

The present invention relates to a gas replacement process, in particular to a degassing process. The present invention also relates to a gas replacement apparatus and use of the gas replacement process or apparatus in the nitro compound hydrogenation reaction process.

BACKGROUND TECHNOLOGY

Aniline is an important basic organic chemical material and a fine chemical intermediate, can be used in producing more than 300 downstream products, and is widely used in the industries of dyes, medicines, pesticides, explosives, spices, rubbers, synthetic materials and the like. In recent years, with the rapid rise of polyurethane industry in China and worldwide, aniline, which is one of the nonreplaceable basic raw material for its main raw material MDI (4,4-diphenylmethane diisocyanate), has been developed remarkably and rapidly.

There are three commercial processes for producing aniline: nitrobenzene catalytic hydrogenation process, phenol ammoniation process and iron powder reduction process. Among others, the iron powder reduction process is gradually eliminated due to poor quality of the formed aniline. The phenol ammoniation process is strongly dependent on the source of the phenol. The current nitrobenzene catalytic hydrogenation process is adopted by most of manufacturers. The nitrobenzene catalytic hydrogenation process is also divided into a gas phase catalytic hydrogenation process and a liquid phase catalytic hydrogenation process. The nitrobenzene liquid phase catalytic hydrogenation process is mainly performed by adopting a noble metal catalyst under an anhydrous condition, and has the advantages of low reaction temperature, high catalyst load, long service life and large plant production capacity, and has the disadvantages of high required pressure, necessary separation of reactants from the catalyst and the solvent, high plant operation cost, high catalyst price, and relatively many byproducts caused by too high catalyst activity. The fluidized bed gas phase catalytic hydrogenation process is characterized by that the nitrobenzene as raw material is heated and vaporized, and mixed with hydrogen gas, then fed into the fluidized bed reactor in which the copper-silica gel catalyst is contained to perform the hydrogenation and reduction reaction. This process has the advantages of better improving the heat transfer condition, controlling the reaction temperature, avoiding the local overheating, reducing the formation of the side reaction, and prolonging the service life of the catalyst, and has the disadvantages of the relatively complicated operation, the heavily worn-out catalyst, and the relatively high operation and maintenance costs. The gas phase hydrogenation process to prepare aniline from nitrobenzene has been used in China for decades, and the fluidized bed gas phase catalytic hydrogenation process is adopted by many aniline manufacturers in China.

Chinese patent application CN1528737A discloses an apparatus, mainly comprising a fluidized bed reactor, a reaction raw material gas inlet arranged at the bottom of the reactor, a first gas distributor arranged at the upper part of the inlet, a second gas distributor arranged at the middle part of the axial-direction height of the reactor and dividing the reactor into two catalyst dense-phase zones, a heat exchanger arranged in two catalyst dense-phase zones inside the reactor; a catalyst overflow device arranged outside or inside the reactor and connecting to the upper and lower two catalyst dense-phase zones respectively, and a gas-solid separation device.

Chinese patent application CN1634860A discloses a gas distributor in a fluidized bed for aniline synthesis and a process for synthesizing aniline, wherein the gas distributor is composed of a main pipe for conveying a gas, branch pipes and an annular pipe connected thereto for distributing the gas, and nozzles for injecting the gas downwards and nozzles for injecting the gas upwards both arranged on the annular pipe.

SUMMARY OF THE INVENTION

The inventors of the present invention have found that in the fluidized bed reactor for preparing aniline in the prior art, reaction gas raw materials enter the fluidized bed from a distributor at the bottom and contact with the catalyst to react and to generate aniline as a product gas, and the catalyst is easy to deposit carbon and deactivate, so that the fluidized bed reactor needs to be stopped for regeneration and activation at intervals and is difficult to operate for a long period. Therefore, the key to solve the problem of long-period operation of the aniline reactor is the capability of completing the regeneration and activation of the aniline catalyst in time and on line. The inventors of the present invention have also found that, in the reaction, regeneration and activation processes, three different components, namely nitrobenzene and hydrogen, oxygen and hydrogen, need to be introduced respectively, wherein when oxygen is in contact with flammable and explosive gases, explosion risks easily occur, therefore after these three stages are finished, each previous stage needs to be efficiently degassed, so that the raw material gas and the product gas entrained in catalyst particles coming from the reactor are effectively removed, the catalyst particles enter the regeneration unit and are regenerated, the air (oxygen) entrained in catalyst particles flowing out of the regenerator is removed, and then the catalyst particles enter the activation unit. The present invention has been completed based on these findings.

Specifically, the present invention relates to the following aspects:

1. A gas replacement (for example stripping or degassing) process, which at least comprises a first step for the gas replacement of a stream to be replaced (for example liquid stream or solid stream, especially solid particle) in the presence of a first replacement gas (for example gas or vapor or steam) (referred to as a first gas replacement step), and then a second step for the gas replacement in the presence of a second replacement gas (for example gas or vapor or steam) (referred to as a second gas replacement step), wherein assuming that the superficial velocity of the first replacement gas (absolute value, the unit is m/s) is V1, and the superficial velocity of the second replacement gas (absolute value, the unit is m/s) is V2, then $V2/V1 \geq 1.5$, $100 \geq V2/V1 \geq 2$, $20 \geq V2/V1 \geq 2.5$ or $15 \geq V2/V1 \geq 5$.

2. The gas replacement process according to any of the above-mentioned or the afterward-mentioned aspects, wherein the first gas replacement step has an operating temperature of 0-700° C. (preferably 80-400° C.), and an operating pressure of 0-3 MPaG (preferably 0.01-1 MPaG), and/or, in the first gas replacement step, the superficial velocity (absolute value) V1 of the first replacement gas is 0.05-0.6 m/s (preferably 0.1-0.3 m/s), and the superficial velocity (absolute value) of the stream to be replaced is 0.02-0.2 m/s (preferably 0.05-0.1 m/s), and/or, the second gas replacement step has an operating temperature of 0-700° C. (preferably 80-400° C.), and an operating pressure of 0-3 MPaG (preferably 0.01-1 MPaG), and/or, in the second gas replacement step, the superficial velocity (absolute value) $V_2$ of the second replacement gas is 0.8-10 m/s (preferably 1-3 m/s), and the superficial velocity (absolute value) of the stream to be replaced is 0.4-6 m/s (preferably 0.6-2.4 m/s).

3. The gas replacement process according to any of the above-mentioned or the afterward-mentioned aspects, wherein in the first gas replacement step, the gas-solid fluidization characteristics is the bubbling or turbulent fluidization, the solid content is in the range of 0.25-0.6, and/or, in the second gas replacement step, the gas-solid fluidization characteristics is the turbulent or fast fluidization, the solid content is in the range of 0.02-0.3.

4. The gas replacement process according to any of the above-mentioned or the afterward-mentioned aspects, wherein the first replacement gas and the stream to be replaced are in countercurrent contact or cocurrent contact (preferably countercurrent contact), and the second replacement gas and the stream to be replaced are in countercurrent contact or cocurrent contact (preferably cocurrent contact).

5. The gas replacement process according to any of the above-mentioned or the afterward-mentioned aspects, wherein the first gas replacement step and the second gas replacement step are carried out in (for example different zones of) one and the same vessel or carried out respectively in different vessels, preferably carried out in (for example different zones of) one and the same vessel, and/or, the first gas replacement step and the second gas replacement step are in the gas-phase communication (especially in the headspace gas-phase communication), and/or, the operating pressure of the first gas replacement step and the operating pressure of the second gas replacement step are basically identical.

6. The gas replacement process according to any of the above-mentioned or the afterward-mentioned aspects, which further comprises one or more gas replacement steps carried out before the first gas replacement step, after the first gas replacement step and before the second gas replacement step, and/or after the second gas replacement step (referred to as additional gas replacement step(s)).

7. A gas replacement apparatus (for example stripper or degassing tank), which at least comprises a first gas replacement region (especially a first vertical gas replacement region) and a second gas replacement region (especially a second vertical gas replacement region) (for example communicated in succession or in series), wherein the inlet for the stream to be replaced of the first gas replacement region is located in the upper part of the first gas replacement region, and the outlet for the replaced stream of the second gas replacement region is located in the upper part of the second gas replacement region; and assuming the cross-sectional area (the unit is m$^2$) of the middle part of the first gas replacement region is A1, and assuming the cross-sectional area (the unit is m$^2$) of the middle part of the second gas replacement region is A2, then $100 \geq A2/A1 \geq 1.5$, $50 \geq A2/A1 \geq 2.5$ or $15 \geq A2/A1 \geq 5$.

8. The gas replacement apparatus according to any of the above-mentioned or the afterward-mentioned aspects, wherein the inlet for the replacement gas of the first gas replacement region is located at the bottom of the first gas replacement region, and the inlet for the replacement gas of the second gas replacement region is located at the bottom of the second gas replacement region, and/or, the outlet for the replaced stream of the first gas replacement region is located at the lower part or the bottom (for example the bottom) of the first gas replacement region, and the inlet for the stream to be replaced of the second gas replacement region (the replaced stream from the previous gas replacement region, for example the replaced stream from the first gas replacement region) is located at the lower part or the bottom (for example the bottom) of the second gas replacement region, and/or, the outlet for the gas phase of the first gas replacement region is located at the top of the first gas replacement region, and the outlet for the gas phase of the second gas replacement region is located at the top of the second gas replacement region.

9. The gas replacement apparatus according to any of the above-mentioned or the afterward-mentioned aspects, wherein the outlet for the gas phase of the first gas replacement region is communicated with the outlet for the gas phase of the second gas replacement region (preferably the outlet for the gas phase of the first gas replacement region is directly communicated with the outlet for the gas phase of the second gas replacement region, more preferably there exists at least one passage between the headspace of the first gas replacement region and the headspace of the second gas replacement region and said at least one passage is configured in such a way that the headspace gas phase of the first gas replacement region enters the headspace of the second gas replacement region and/or the headspace gas phase of the second gas replacement region enters the headspace of the first gas replacement region, more preferably the first gas replacement region and the second gas replacement region share a headspace), and/or, the outlet for the replaced stream of the first gas replacement region is communicated with the inlet for the stream to be replaced of the second gas replacement region (preferably the outlet for the replaced stream of the first gas replacement region is directly communicated with the inlet for the stream to be replaced of the second gas replacement region, more preferably there exists at least one passage between the first gas replacement region and the second gas replacement region, and said at least one passage is configured in such a way that the replaced stream of the first gas replacement region enters the second gas replacement region as the stream to be replaced).

10. The gas replacement apparatus according to any of the above-mentioned or the afterward-mentioned aspects, wherein the first gas replacement region and the second gas replacement region are separately located in different vessels (for example different strippers or degassing tanks), or the first gas replacement region and the second gas replacement region are together located in one and the same vessel (for example located in one and the same stripper or degassing tank), and/or, the first gas replacement region and the second gas replacement region are together located in one and the same vessel, and there exists at least one partition structural member (for example a plate or ring-shaped partition structural member) between the first gas replacement region and the second gas replacement region.

11. The gas replacement apparatus according to any of the above-mentioned or the afterward-mentioned aspects, wherein the central axis direction of the first gas replacement region is substantially parallel to the central axis direction of the second gas replacement region, and/or, in a direction perpendicular to the horizontal plane, the inlet for the replacement gas of the first gas replacement region is substantially at the same level as or above the inlet for the replacement gas of the second gas replacement region or the bottom of the first gas replacement region is substantially at the same level as or above the bottom of the second gas replacement region.

12. The gas replacement apparatus according to any of the above-mentioned or the afterward-mentioned aspects, which further comprises one or more gas replacement regions (referred to as additional gas replacement region(s)) before the first gas replacement region, after the first gas replacement region and before the second gas replacement region, and/or after the second gas replacement region.

13. The gas replacement apparatus according to any of the above-mentioned or the afterward-mentioned aspects, wherein a flow disturbance structural member is disposed in the first gas replacement region and/or the second gas replacement region and/or the additional gas replacement region, the flow disturbance structural member comprises at least one (for example 1-1000 or 4-100) flow rectifier(s) (for example selected from at least one of a streamline flow rectifier, a diamond-shaped flow rectifier and an inclined baffle cross-flow type flow rectifier) and a connecting piece for fixing said at least one flow rectifier relative to the corresponding gas replacement region (for example the first gas replacement region or the second gas replacement region) and/or relative to each other (when a plurality of the flow rectifiers are present).

14. The gas replacement apparatus according to any of the above-mentioned or the afterward-mentioned aspects, wherein the streamline flow rectifier is selected from at least one of a combination of two semiellipsoids, a combination of one semiellipsoid and one cone, a combination of one semiellipsoid and one circular arc streamlined body and a combination of one semiellipsoid and one paraboloid, preferably a combination of one semiellipsoid and one paraboloid, and/or, the diamond-shaped flow rectifier is selected from at least one of a combination of two pyramids, a combination of two prismoids, and a combination of one pyramid and one prismoid, preferably a combination of two pyramids, and/or, the inclined baffle cross-flow type flow rectifier is a baffle inclined with respect to a horizontal plane (for example the angle of inclination with respect to a horizontal plane is 0-60°, preferably 10-40°).

15. The gas replacement apparatus according to any of the above-mentioned or the afterward-mentioned aspects, wherein the central axis direction of said at least one flow rectifier substantially conforms to the central axis direction of the corresponding gas replacement region (for example the first gas replacement region or the second gas replacement region), and/or, at least one of said flow rectifiers has at least one run-through flow passage (for example through hole) (preferably disposed along the central axis direction of the corresponding gas replacement region (for example the first gas replacement region or the second gas replacement region)), preferably the ratio of the cross-sectional area of the run-through flow channel (in case that a plurality of said run-through flow channels are present, the sum of the cross-sectional areas of the multiple run-through flow channels, the unit is $m^2$) to the maximum cross-sectional area of the corresponding flow rectifier (the unit is $m^2$) is 1-30:100 or 3-15:100, and/or, in each flow disturbance structural member, the ratio of the maximum cross-sectional area of the flow rectifier (when a plurality of the flow rectifiers are present, the sum of the maximum cross-sectional areas of the multiple flow rectifiers, the unit is $m^2$) to the corresponding cross-sectional area (the unit is $m^2$) of the corresponding gas replacement region (for example the first gas replacement region or the second gas replacement region) is 20-90:100 (preferably 45-65:100), and/or, in each flow disturbance structural member, when a plurality of the flow rectifiers are present, said the multiple flow rectifiers are arranged in a predetermined manner (for example arranged in a random, triangular, square, rectangular, circular or annular manner) in relation to one another, and/or, one or more (for example 2-20 or 4-10) said flow disturbance structural members are disposed along the central axis direction of the corresponding gas replacement region (for example the first gas replacement region or the second gas replacement region), and/or, the vertical distance (the unit is m) of any two adjacent flow disturbance structural members in relation to one another along the central axis direction of the corresponding gas replacement region (for example the first gas replacement region or the second gas replacement region) is 2% H-20% H, wherein H is the height (the unit is m) of the corresponding gas replacement region (for example the first gas replacement region or the second gas replacement region), and/or, assuming the height of the first gas replacement region (the unit is m) is H1, assuming the height of the second gas replacement region (the unit is m) is H2, then H2/H1≥1 or 2≥H2/H1≥1.

16. A reaction system (especially a nitro compound hydrogenation reaction system), comprising at least one reactor (preferably a fluidized bed reactor, especially a reactor having the fluidized bed of catalyst particles) and at least one (for example 1-3 or 2) gas replacement apparatus communicated with (for example communicated downstream with) said at least one reactor (for example configured to receive an effluent from said at least one reactor, especially configured to receive the spent catalyst particles from said at least one reactor), wherein at least one of the gas replacement apparatuses is configured to implement the gas replacement apparatus of the gas replacement process according to any of the above-mentioned or the afterward-mentioned aspects or is the gas replacement apparatus according to any of the above-mentioned or the afterward-mentioned aspects.

17. A nitro compound hydrogenation reaction process, at least comprising a step of contacting a nitro compound (especially nitrobenzene) as the reaction raw material with hydrogen gas and a hydrogenation catalyst to obtain a reaction product (for example an amino compound, especially aniline) and a spent catalyst (referred to as a hydrogenation reaction step) and a step of subjecting the spent catalyst to the gas replacement (for example degassing) in the presence of a replacement gas (referred to as the gas replacement step), wherein the gas replacement step is proceeded according to the gas replacement process according to any of the above-mentioned or the afterward-mentioned aspects or proceeded in the gas replacement apparatus according to any of the above-mentioned or the afterward-mentioned aspects.

18. The hydrogenation reaction process according to any of the above-mentioned or the afterward-mentioned aspects, wherein the reaction conditions of the hydrogenation reaction step comprise: the superficial gas velocity is 0.2-0.8 m/s, the molar ratio of hydrogen gas to the reaction raw material (for example nitrobenzene) is 6-21, the reaction temperature is 220-280° C., the reaction pressure is 0.05-1 MPa (gauge pressure), the hydrogenation catalyst is selected from at least one of a copper-based loaded catalyst, a nickel-based loaded catalyst and a noble metal-based loaded catalyst, and/or, the bulk density of the hydrogenation catalyst is 300-1200 kg/$m^3$, and/or, the average particle diameter of the hydrogenation catalyst is 30-800 μm (preferably 40-500 μm or 50-600 μm), and the mass percent of the catalyst particles having a particle diameter of less than 80

μm to the whole catalyst particles is not less than 2 wt % (preferably 5-15 wt %), and/or, the replacement gas is a gas or a vapor (especially selected from at least one of nitrogen gas, water vapor, carbon dioxide, methane, oxygen gas and argon gas), and/or, the nitro compound is selected from at least one of the compounds represented by the following formula (1),

$$R\text{—}NO_2 \quad (1)$$

In the structural formula (1), R is an optionally substituted $C_{2\text{-}20}$ straight, branched or cyclic hydrocarbyl (preferably an optionally substituted $C_{4\text{-}20}$ cyclic hydrocarbyl, especially an optionally substituted $C_{6\text{-}20}$ aryl, more especially an optionally substituted phenyl).

On the other hand, the present invention relates to the following aspects:

1. A reaction apparatus for producing aniline by the nitrobenzene hydrogenation, comprising: a fluidized bed reactor (3), a degassing tank for the spent catalyst (12), a regenerator (13), a degassing tank for the catalyst to be activated (16), an activator (19) and a lifting pipe (21), wherein a dense phase reaction zone (4) located in the lower section, a particle sputtering transition zone (5) located in the middle section and a dilute-phase zone (7) located in the upper section are included in the fluidized bed reactor (3), the degassing tank for the spent catalyst (12) is communicated with the fluidized bed reactor (3) and the regenerator (13) respectively, the degassing tank for the catalyst to be activated (16) is communicated with the regenerator (13) and the activator (19) respectively, a lifting pipe (21) is communicated with the activator (19) and the fluidized bed reactor (3) respectively.

2. The reaction apparatus for producing aniline by the nitrobenzene hydrogenation according to any of the above-mentioned or the afterward-mentioned aspects, which is characterized in that in the fluidized bed reactor (3) are provided a gas distributor (2), a heat-exchanging pipe (11), a sputtering separation structural member (6) and a cyclone separator (9).

3. The reaction apparatus for producing aniline by the nitrobenzene hydrogenation according to any of the above-mentioned or the afterward-mentioned aspects, which is characterized in that in the degassing tank for the spent catalyst (12) are included a degassing descending countercurrent zone (31) and a degassing ascending co-current zone (32), and in the degassing descending countercurrent zone (31) and the degassing ascending co-current zone (32) are respectively provided degassing baffle structural members (33); in the degassing tank for the catalyst to be activated (16) are included a regeneration degassing descending countercurrent zone (51) and a regeneration degassing ascending co-current zone (52), and in the regeneration degassing descending countercurrent zone (51) and the regeneration degassing ascending co-current zone (52) are respectively provided degassing baffle structural members (33).

4. The reaction apparatus for producing aniline by the nitrobenzene hydrogenation according to any of the above-mentioned or the afterward-mentioned aspects, which is characterized in that the degassing baffle structural member (33) is made by connecting multiple sets of flow rectifiers through connecting pieces, the flow rectifier is one or more of a streamline flow rectifier (41), a diamond-shaped flow rectifier (42), and an inclined baffle cross-flow type flow rectifier (43).

5. A reaction process for producing aniline by the nitrobenzene hydrogenation with the apparatus according to any of the above-mentioned or the afterward-mentioned aspects, comprising the following steps:

(a). Vaporized nitrobenzene and hydrogen gas as raw material are introduced into a gas chamber, then into the fluidized bed reactor (3) through the gas distributor (2) to push the catalyst in the reactor to be fluidized, then react in the dense phase reaction zone (4) to produce an aniline product, the particle sputtering occurs at the top of the dense phase reaction zone (4) to form a particle sputtering transition zone (5), the sputtered particles are efficiently intercepted by the sputtering separation structural member (6) and return to the dense phase reaction zone (4) to proceed with the catalysis, a small part of the non-intercepted particles pass through the passage of the sputtering separation structural member and enter the dilute-phase zone (7) to be separated with a cyclone separator (9), the particles return to the dense phase reaction zone (4), the crude product gas (8) flows out of the fluidized bed reactor (3) and is sent into the subsequent separation section;

(b). After the catalyst is partly coked in the reaction, the coked catalyst is degassed in the degassing tank for the spent catalyst (12), and introduced into the regenerator (13), to which the oxygen is introduced, the catalyst is regenerated by carbon burning;

(c). The regenerated catalyst is then introduced into the degassing tank for the catalyst to be activated (16) and degassed, and then introduced into the activator (19), to which hydrogen gas is introduced, the catalyst is activated, and the activated catalyst is introduced into the lifting pipe (21), and lifted up to return to the fluidized bed reactor (3) to proceed with the catalysis.

6. The reaction process for producing aniline by the nitrobenzene hydrogenation according to any of the above-mentioned or the afterward-mentioned aspects, which is characterized in that the catalyst is a metal loaded catalyst with copper as the main active component, the support is alumina or silica, the catalyst had an average particle diameter of 50-600 μm, and the content of particles lower than 80 μm is not less than 2%.

7. The reaction process for producing aniline by the nitrobenzene hydrogenation according to any of the above-mentioned or the afterward-mentioned aspects, which is characterized in that the reaction conditions in the fluidized bed reactor (3) comprise: the superficial gas velocity is 0.2-0.8 m/s, the molar ratio of hydrogen gas to nitrobenzene is 6-21, the average reaction temperature in the dense phase reaction zone (4) is controlled at 220-280° C., the temperature in the vicinity of the gas distributor (2) is controlled at 320° C. or less, the reaction pressure in the dense phase reaction zone (4) is 0.05-1 MPa.

8. The reaction process for producing aniline by the nitrobenzene hydrogenation according to any of the above-mentioned or the afterward-mentioned aspects, which is characterized in that the reaction conditions in the regenerator (13) comprise: the superficial gas velocity is 0.1-0.6 m/s, and the average regeneration temperature is 350-450° C.; the reaction conditions in the activator (19) comprise: the superficial gas velocity is 0.1-0.6 m/s, and the average activation temperature is 200-250° C.

9. The reaction process for producing aniline by the nitrobenzene hydrogenation according to any of the above-mentioned or the afterward-mentioned aspects, which is characterized in that the ratio of the superficial gas velocity of the degassing descending countercurrent zone (31) to the superficial gas velocity of the degassing ascending cocurrent zone (32) in the degassing tank for the spent catalyst (12) is 1/15-1, the degassing agent is one or more (as mixture) of nitrogen gas, water vapor, carbon dioxide, methane, and argon gas, the gas component carried over from the fluidized bed reactor (3) is replaced out.

10. The reaction process for producing aniline by the nitrobenzene hydrogenation according to any of the above-mentioned or the afterward-mentioned aspects, which is characterized in that the ratio of the superficial gas velocity of the regeneration degassing descending countercurrent zone (51) to the superficial gas velocity of the regeneration degassing ascending co-current zone (52) in the degassing tank for the catalyst to be activated (16) is 1/15-1, the degassing agent is one or more (as mixture) of nitrogen gas, water vapor, carbon dioxide, oxygen gas, and argon gas, the oxygen-containing gas component carried over from the regenerator (13) is replaced out.

Technical Effect

According to the gas replacement process or the gas replacement apparatus of the present invention, the gas replacement efficiency (especially degassing efficiency) generally can reach 90% or higher, preferably 94% or higher.

The gas replacement process or the gas replacement apparatus according to the present invention, when used in the hydrogenation reaction of the nitro compound (for example the nitrobenzene hydrogenation to produce aniline), can achieve the purpose of the long-time cycle production of the continuous reaction, regeneration and activation, and at the same time can also achieve the technical effects such as the improved degassing efficiency (for example, the increase by 7% or higher) and the controllable carbon deposition amount on the catalyst in the fluidized bed reactor.

BRIEF DESCRIPTION OF THE DRAWINGS

In FIG. 1, 1: raw material of vaporized nitrobenzene and hydrogen gas; 2: gas distributor; 3: fluidized bed reactor; 4: dense-phase reaction zone; 7: dilute-phase zone; 8: crude product gas; 9: cyclone separator; 10: dipleg; 11: heat-exchanging pipe; 12: degassing tank for the spent catalyst; 13: regenerator; 15: fluidization gas for regeneration; 16: degassing tank for the catalyst to be activated; 17: fluidization gas for activation; 19: activator; 20: lifting gas; 21: lifting pipe. Herein, the degassing tank for the spent catalyst or the degassing tank for the catalyst to be activated is the gas replacement apparatus of the present invention or the gas replacement process of the present invention is implemented therein.

In FIG. 2, 21 represents the first gas replacement step, 22 represents the second gas replacement step, and both of them are separated by a partition. In addition, the solid triangle arrow represents the main flow direction of the replacement gas; the hollow triangle arrow represents the main flow direction of the stream to be replaced, for example the solid particles. The superficial velocity of the first replacement gas is expressed as V1, and the superficial velocity of the second replacement gas is expressed as V2. According to circumstances, the first gas replacement step and/or the second gas replacement step can be performed in the presence of the flow disturbance structural members (the number in the figure: 4, for example, the flow disturbance structural member 33 described below in the present invention).

FIG. 3, 30: the partition structural member; 31: the first gas replacement region; 321: the second gas replacement region; 33: the flow disturbance structural member (the number in the figure: 4); 34: the inlet for the stream to be replaced of the first gas replacement region; 35: the outlet for the replaced stream of the second gas replacement region; 36: the inlet for the stream to be replaced of the second gas replacement region; 37: the outlet for the replaced stream of the first gas replacement region; 38: the outlet for the gas phase of the first gas replacement region; 39: the outlet for the gas phase of the second gas replacement region; 40: the shared headspace; 41: the flow rectifier (the number in the figure: more than one). In addition, the solid triangle arrow represents the main flow direction of the replacement gas; the hollow triangle arrow represents the main flow direction of the stream to be replaced, for example the solid particles. The cross-sectional area of the middle part of the first gas replacement region is expressed as A1, and the cross-sectional area of the middle part of the second gas replacement region is expressed as A2.

DETAILED DESCRIPTION

Figure 1:
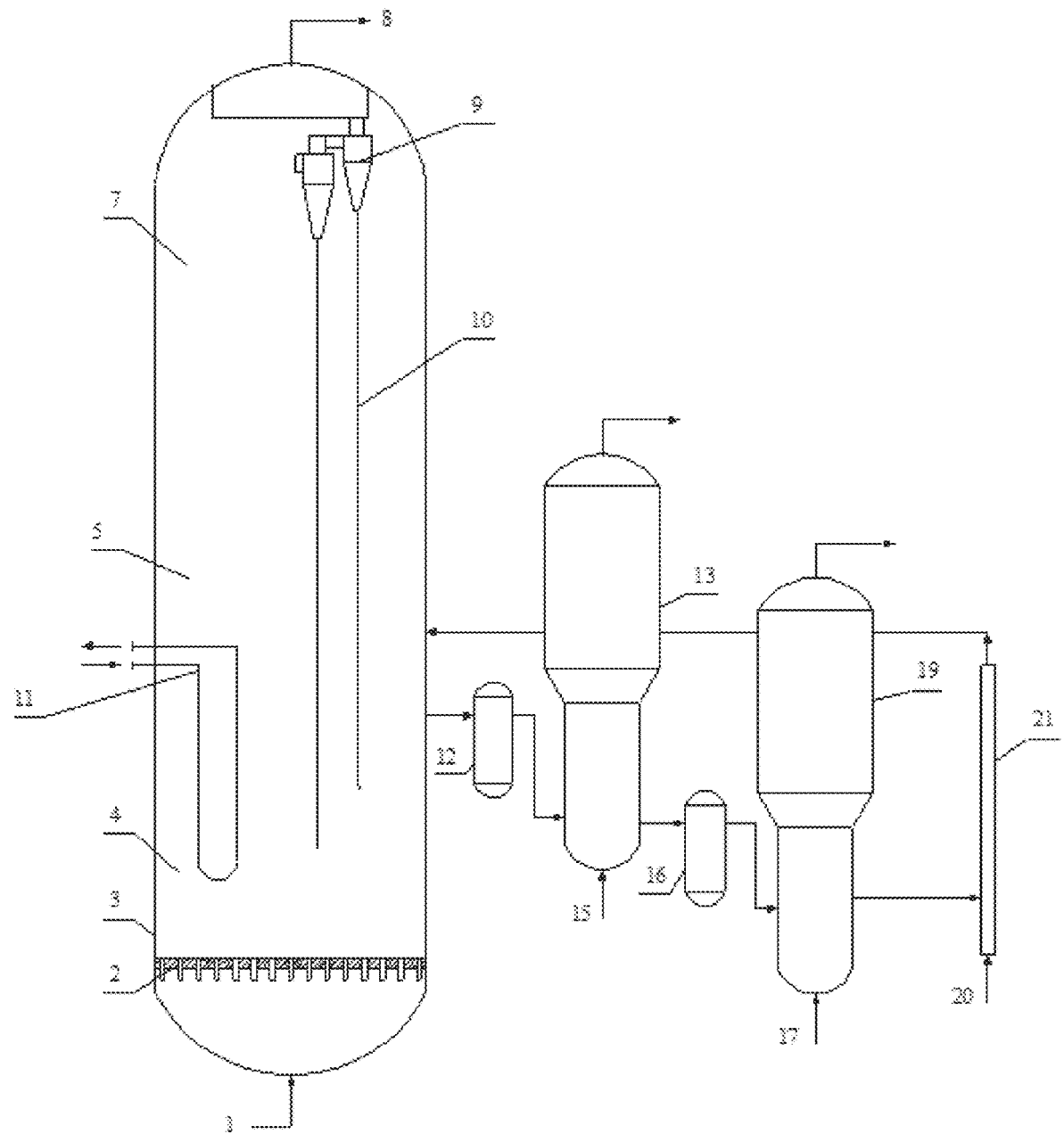
FIG. 1 is a schematic flow diagram of the hydrogenation reaction system of the nitro compound of the present invention, in which the nitrobenzene hydrogenation to produce aniline is taken as an example.

Reference will now be made in detail to the present embodiments of the present invention, but it should be understood that the scope of the invention is not limited by the embodiments, but is defined by the appended claims.

All publications, patent applications, patents, and other references mentioned in this specification are herein incorporated by reference in their entirety. Unless defined otherwise, all technical and scientific terms used herein have the same meanings as commonly understood by those skilled in the art to which this invention belongs. In case of conflict, the present specification, including definitions, will control.

When the specification derives a material, a substance, a process, a step, a device, an element and the like with the expression such as "known to those skilled in the art", "prior art", or the anologous term, it is intended that the subject matter so derived encompasses those having been conventionally used in the art at the time of filing this application, but also includes those which may not be so commonly used at the present time, but will become known in the art as being suitable for a similar purpose.

In the context of the present specification, the term "substantially" means the allowance of the presence of a deviation acceptable to those skilled in the art or considered reasonable by those skilled in the art, for example, a deviation within ±10%, within ±5%, within ±1%, within ±0.5% or within ±0.1%.

In the context of the present specification, the term "gas replacement" refers to the replacement of gaseous substances or easily vaporizable substances (collectively referred to as hazardous substances) contained in a stream (referred to as the stream to be replaced) with a gas (referred to as the replacement gas) to remove the hazardous substances from the stream to be replaced. Herein, the gas replacement generally includes degassing, steam stripping and the like, particularly refers to degassing.

In the context of the present specification, the gas replacement efficiency (for example the degassing efficiency) refers to the ratio of the gas amount of the replacement gas (for example the degassing agent) remaining in the gas replacement apparatus (for example the degassing tank) after the gas replacement is completed to the total amount of all gases in the gas replacement apparatus. The closer the gas replacement efficiency is to 1, the better the effect of the gas replacement is. Herein, as the measuring method for the gas replacement efficiency, for example, a method of analyzing the ratio of the gas amount of the replacement gas to the total amount of all gases in the gas replacement apparatus with a gas analysis instrument such as a gas phase chromatography, can be enumerated.

In the context of the present specification, the term "superficial velocity" refers to the speed at which a gas flows through a certain region without considering the solid such as solid catalyst particles, which can be obtained by dividing the flow rate per unit time through the region by the cross-sectional area of the region.

In the context of the present specification, the term "solid content" refers to the volume fraction of solid particles in the gas-solid two-phase mixture. The solid content at an arbitrary position can be calculated by the equation $$\frac{\Delta P}{\Delta z} \approx [\rho_P(1-\varepsilon) + \rho\varepsilon]g,$$

wherein $\Delta P$ is the difference (the unit is Pa) between the pressure (gauge pressure) at $\Delta z/2$ below the position and the pressure (gauge pressure) at $\Delta z/2$ above the position, $\Delta z$ is the distance (the unit is m) between the point at $\Delta z/2$ below the position and the point at $\Delta z/2$ above the position, $\rho p$ is the particle density (the unit is kg/m$^3$) of the solid particles, p is the density (the unit is kg/m$^3$) of the gas, 1-$\varepsilon$ is the solid content, $\varepsilon$ is the gas content, the sum of the solid content and the gas content is 1, g is the absolute value of the gravity acceleration (generally taking 9.8 m/s$^2$).

In the context of the present specification, the term "vertical" means that the central axis is substantially perpendicular to the horizontal plane.

In the context of the present specification, assuming that along the central axis direction of a certain gas replacement region, the vertical distance (the unit is m) from the bottom of the gas replacement region to the top of the gas replacement region is H, then the part between for example 25% H above and below the ½H location point is referred to as the middle part, the part between the middle part and the top is referred to as the upper part, and the part between the middle part and the bottom is referred to as the lower part.

In the context of the present specification, the expression "optionally substituted" refers to being optionally substituted by one or more (for example 1-5, 1-4, 1-3, 1-2 or 1) substituent groups selected from halogen, hydroxy, mercapto, amino, aminocarbonyl, nitro, oxo, thio, cyano, $C_{1-6}$ linear or branched (halo) alkane (oxy, thio, amino, carbonyl) group, $C_{2-6}$ linear or branched (halo) alkene (oxy, thio, amino, carbonyl) group, $C_{2-6}$ linear or branched (halo) alkyne (oxy, thio, amino, carbonyl) group, $C_{3-20}$ cycloalkyl, $C_{3-20}$ cycloalkane (oxy, thio, amino) group, $C_{3-20}$ cycloalkyl $C_{1-6}$ linear or branched (halo) alkane (oxy, thio, amino, carbonyl) group, $C_{3-20}$ cycloalkyl $C_{2-6}$ linear or branched (halo) alkene (oxy, thio, amino, carbonyl) group, $C_{3-20}$ cycloalkyl $C_{2-6}$ linear or branched (halo) alkyne (oxy, thio, amino, carbonyl) group, $C_{3-20}$ cycloalkenyl, $C_{3-20}$ cycloalkene (oxy, thio, amino) group, $C_{3-20}$ cycloalkenyl $C_{1-6}$ linear or branched (halo) alkane (oxy, thio, amino, carbonyl) group, $C_{3-20}$ cycloalkenyl $C_{2-6}$ linear or branched (halo) alkene (oxy, thio, amino, carbonyl) group, $C_{3-20}$ cycloalkenyl $C_{2-6}$ linear or branched (halo) alkyne (oxy, thio, amino, carbonyl) group, $C_{6-20}$ aryl, $C_{6-20}$ arene (oxy, thio, amino) group, $C_{6-20}$ aryl $C_{1-6}$ linear or branched (halo) alkane (oxy, thio, amino, carbonyl) group, $C_{6-20}$ aryl $C_{2-6}$ linear or branched (halo) alkene (oxy, thio, amino, carbonyl) group, $C_{6-20}$ aryl $C_{2-6}$ linear or branched (halo) alkyne (oxy, thio, amino, carbonyl) group, $C_{4-20}$ heteroaryl, $C_{4-20}$ heteroarene (oxy, thio, amino) group, $C_{4-20}$ heteroaryl $C_{1-6}$ linear or branched (halo) alkane (oxy, thio, amino, carbonyl) group, $C_{4-20}$ heteroaryl $C_{2-6}$ linear or branched (halo) alkene (oxy, thio, amino, carbonyl) group, $C_{4-20}$ heteroaryl $C_{2-6}$ linear or branched (halo) alkyne (oxy, thio, amino, carbonyl) group, $C_{2-20}$ heterocyclyl, $C_{2-20}$ heterocycle (oxy, thio, amino) group, $C_{2-20}$ heterocyclyl $C_{1-6}$ linear or branched (halo) alkane (oxy, thio, amino, carbonyl) group, $C_{2-20}$ heterocyclyl $C_{2-6}$ linear or branched (halo) alkene (oxy, thio, amino, carbonyl) group and $C_{2-20}$ heterocyclyl $C_{2-6}$ linear or branched (halo) alkyne (oxy, thio, amino, carbonyl) group. When a plurality of these substituent groups are present, two adjacent substituent groups (for example the molecular chain ends of two substituent groups) can be bonded to each other to form a divalent substituent group structure. For example, two adjacent $C_{1-6}$ linear or branched alkyl groups can be bonded to each other to form a corresponding alkylene structure. Or, two adjacent $C_{1-6}$ linear or branched alkyloxy groups for example can form a corresponding alkylenedioxy group structure, two adjacent $C_{1-6}$ linear or branched alkylamino groups for example can form a corresponding alkylenediamino structure, two adjacent $C_{1-5}$ linear or branched alkylthio groups for example can form a corresponding alkylenedithio structure, and so forth. As the preferred substituent group, for example, halogen, hydroxy, mercapto, amino, thio, oxo or $C_{1-6}$ linear or branched (halo) alkane (oxy, thio, amino, carbonyl) group and others can be enumerated. Herein, the expression "(halo) alkane (oxy, thio, amino, carbonyl) group" means: alkyl, haloalkyl, alkyloxy, alkylthio, alkylamino, alkylcarbonyl, haloalkyloxy, haloalkylthio, haloalkylamino or haloalkylcarbonyl, the expression "(halo) alkene (oxy, thio, amino, carbonyl) group" means: alkenyl, haloalkenyl, alkenyloxy, alkenylthio, alkenylamino, alkenylcarbonyl, haloalkenyloxy, haloalkenylthio, haloalkenylamino or haloalkenylcarbonyl, the expression "(halo) alkyne (oxy, thio, amino, carbonyl) group" means: alkynyl, haloalkynyl, alkynyloxy, alkynylthio, alkynylamino, alkynylcarbonyl, haloalkynyloxy, haloalkynylthio, haloalkynylamino or haloalkynylcarbonyl, the expression "(oxy, thio, amino) group" means oxy, thio or amino. Here, the expression "halo" includes monohalo, dihalo, trihalo, or perhalo, and the like.

All percentages, parts, ratios, and the like referred to within this specification are by weight and pressures are gauge pressures unless explicitly indicated.

In the context of this specification, any two or more embodiments of the present invention may be combined in any combination, and the resulting technical solution is part of the original disclosure of this specification, and is within the scope of the present invention.

According to one embodiment of the present invention, it relates to a gas replacement process. As the gas replacement process, for example, steam stripping or degassing, especially degassing can be enumerated.

According to one embodiment of the present invention, the gas replacement process at least comprises a first step of subjecting a stream to be replaced to the gas replacement in presence of a first replacement gas (referred to as a first gas replacement step), and then a second step of subjecting to the gas replacement in presence of the second replacement gas (referred to as a second gas replacement step). Herein, as the stream to be replaced, for example a liquid stream or a solid stream can be enumerated, especially solid particles, more especially solid catalyst particles, even more especially solid catalyst particles having a particle average diameter of 30-800 μm. In addition, the particle average diameter is preferably 40-500 μm or 50-600 μm. For example, the particle average diameter can be obtained by the analysis of the sampled solid catalyst particles with a particle-size analyzer.

According to one embodiment of the present invention, the first replacement gas and the second replacement gas are, identical to or different from each other, each independently selected from any gas or vapor or steam that can be used during the gas replacement (especially degassing) in the art, for example, nitrogen gas, water vapor, carbon dioxide, methane, oxygen gas, argon gas, air or hydrogen gas and the like can be specifically enumerated without particular limitation.

According to one embodiment of the present invention, the gas replacement process further comprises one or more gas replacement steps carried out before the first gas replacement step, after the first gas replacement step and before the second gas replacement step, and/or after the second gas replacement step (referred to as additional gas replacement step(s)). To this end, although the first gas replacement step and the second gas replacement step are performed in the successive order, one or more additional gas replacement steps may sometimes be inserted between these two steps according to circumstances. Herein, as the additional gas replacement step, it can be performed according to any manner known in the art, or can be performed according to the first gas replacement step or according to the second gas replacement step, without particular limitation. Preferably, the first gas replacement step and the second gas replacement step are directly performed in succession. That is to say, no other gas replacement step is inserted between the first gas replacement step and the second gas replacement step, and the stream to be replaced is passed through the first gas replacement step and the second gas replacement step and the gas replacement is continuously performed.

According to one embodiment of the present invention, assuming the superficial velocity of the first replacement gas (absolute value, the unit is m/s) is V1, the superficial velocity of the second replacement gas (absolute value, the unit is m/s) is V2, then $V2/V1 \geq 1.5$. Preferably, $100 \geq V2/V1 \geq 2$ or $20 \geq V2/V1 \geq 2.5$, especially $15 \geq V2/V1 \geq 5$.

According to one embodiment of the present invention, the operating temperature of the first gas replacement step is not particularly limited, but is generally 0-700° C., preferably 80-400° C.

According to one embodiment of the present invention, the operating pressure of the first gas replacement step is not particularly limited, but is generally 0-3 MPaG, preferably 0.01-1 MPaG.

According to one embodiment of the present invention, in the first gas replacement step, the superficial velocity of the first replacement gas (absolute value) V1 is generally 0.05-0.6 m/s, preferably 0.1-0.3 m/s.

According to one embodiment of the present invention, in the first gas replacement step, the superficial velocity of the stream to be replaced (absolute value) is generally 0.02-0.2 m/s, preferably 0.05-0.1 m/s.

According to one embodiment of the present invention, the operating temperature of the second gas replacement step is not particularly limited, but is generally 0-700° C., preferably 80-400° C.

According to one embodiment of the present invention, the operating pressure of the second gas replacement step is not particularly limited, but is generally 0-3 MPaG, preferably 0.01-1 MPaG.

According to one embodiment of the present invention, in the second gas replacement step, the superficial velocity of the second replacement gas (absolute value) V2 is generally 0.8-10 m/s, preferably 1-3 m/s.

According to one embodiment of the present invention, in the second gas replacement step, the superficial velocity of the stream to be replaced (absolute value) is generally 0.4-6 m/s, preferably 0.6-2.4 m/s.

According to one embodiment of the present invention, in the first gas replacement step, the gas-solid fluidization is characterized in bubbling or turbulent fluidization, and the solid content rate is generally in the range of 0.25-0.6.

According to one embodiment of the present invention, in the second gas replacement step, the gas-solid fluidization is characterized in turbulent or fast fluidization, and the solid content rate is generally in the range of 0.02-0.3.

According to one embodiment of the present invention, the first replacement gas and the stream to be replaced are in countercurrent contact or cocurrent contact, preferably countercurrent contact.

According to one embodiment of the present invention, the second replacement gas and the stream to be replaced are in countercurrent contact or cocurrent contact, preferably cocurrent contact.

According to one embodiment of the present invention, the first gas replacement step and the second gas replacement step are carried out in (for example different zones of) one and the same vessel or carried out in different vessels respectively. Herein, the first gas replacement step and the second gas replacement step are preferably carried out in (for example different zones of) one and the same vessel.

According to one embodiment of the present invention, the first gas replacement step and the second gas replacement step are in the gas-phase communication, especially in the headspace gas-phase communication. To this end, preferably, the operating pressure of the first gas replacement step and the operating pressure of the second gas replacement step are basically identical.

According to one embodiment of the present invention, it also relates to a gas replacement apparatus. Herein, as the gas replacement apparatus, for example, stripper or degassing tank, especially degassing tank can be specifically enumerated.

According to one embodiment of the present invention, the gas replacement apparatus at least comprises a first gas replacement region and a second gas replacement region. Herein, the first gas replacement region and the second gas replacement region can be communicated according to any manner known in the art, and for example, the communication in succession or in series can be specifically enumerated. In addition, the first vertical gas replacement region can be particularly enumerated as the first gas replacement region; or the second vertical gas replacement region can be particularly enumerated as the second gas replacement region.

According to one embodiment of the present invention, the operation conditions of the first gas replacement region are not particularly limited, those well known in the art can be directly applied, for example the operating temperature is generally 0-700° C., preferably 80-400° C., the operating pressure is generally 0-3 MPaG, preferably 0.01-1 MPaG.

According to one embodiment of the present invention, the superficial velocity of the replacement gas in the first gas replacement region is not particularly limited, those well known in the art can be directly applied, for example the superficial velocity (absolute value) is generally 0.05-0.6 m/s, preferably 0.1-0.3 m/s.

According to one embodiment of the present invention, the operation conditions of the second gas replacement region are not particularly limited, those well known in the art can be directly applied, for example the operating temperature is generally 0-700° C., preferably 80-400° C., the operating pressure is generally 0-3 MPaG, preferably 0.01-1 MPaG.

According to one embodiment of the present invention, the superficial velocity of the replacement gas in the second gas replacement region is not particularly limited, those well known in the art can be directly applied, for example the superficial velocity (absolute value) is generally 0.05-10 m/s, 0.1-10 m/s or 0.8-10 m/s, preferably 1-3 m/s.

According to one embodiment of the present invention, the gas replacement process implemented in the first gas replacement region is not particularly limited, and can be performed according to any manner known in the art, but preferably proceeded according to the first gas replacement step mentioned in any of the previous embodiments of the present invention.

According to one embodiment of the present invention, the gas replacement process implemented in the second gas replacement region is not particularly limited, and can be performed according to any manner known in the art, but preferably proceeded according to the second gas replacement step mentioned in any of the previous embodiments of the present invention.

According to one embodiment of the present invention, the inlet for the stream to be replaced of the first gas replacement region is located in the upper part of the first gas replacement region, and the outlet for the replaced stream of the second gas replacement region is located in the upper part of the second gas replacement region.

According to one embodiment of the present invention, assuming the cross-sectional area (the unit is $m^2$) of the middle part of the first gas replacement region is A1, assuming the cross-sectional area (the unit is $m^2$) of the middle part of the second gas replacement region is A2, then $100 \geq A2/A1 \geq 1.5$. Preferably, $50 \geq A2/A1 \geq 2.5$ or $15 \geq A2/A1 \geq 5$.

According to one embodiment of the present invention, the inlet for the replacement gas of the first gas replacement region is located at the bottom of the first gas replacement region, the inlet for the replacement gas of the second gas replacement region is located at the bottom of the second gas replacement region.

According to one embodiment of the present invention, the outlet for the replaced stream of the first gas replacement region is located at the lower part or the bottom, especially the bottom of the first gas replacement region. The inlet for the stream to be replaced of the second gas replacement region is located at the lower part or the bottom, especially the bottom of the second gas replacement region. Herein, the stream to be replaced corresponds to the replaced material from the previous gas replacement region, for example the replaced stream from the first gas replacement region.

According to one embodiment of the present invention, the outlet for the gas phase of the first gas replacement region is located at the top of the first gas replacement region, and the outlet for the gas phase of the second gas replacement region is located at the top of the second gas replacement region.

According to one embodiment of the present invention, the outlet for the gas phase of the first gas replacement region is communicated with the outlet for the gas phase of the second gas replacement region. Preferably, the outlet for the gas phase of the first gas replacement region is directly communicated with the outlet for the gas phase of the second gas replacement region, more preferably there exists at least one passage between the headspace of the first gas replacement region and the headspace of the second gas replacement region and said at least one passage is configured in such a way that the headspace gas phase of the first gas replacement region enters the headspace of the second gas replacement region and/or the headspace gas phase of the second gas replacement region enters the headspace of the first gas replacement region, more preferably the first gas replacement region and the second gas replacement region share a headspace.

According to one embodiment of the present invention, the outlet for the replaced stream of the first gas replacement region is communicated with the inlet for the stream to be replaced of the second gas replacement region. Preferably, the outlet for the replaced stream of the first gas replacement region is directly communicated with the inlet for the stream to be replaced of the second gas replacement region, more preferably there exists at least one passage between the first gas replacement region and the second gas replacement region, and said at least one passage is configured in such a way that the replaced stream of the first gas replacement region enters the second gas replacement region as the stream to be replaced.

According to one embodiment of the present invention, the first gas replacement region and the second gas replacement region are located in different vessels respectively, for example located in different strippers or degassing tanks respectively. Or, the first gas replacement region and the second gas replacement region are together located in one and the same vessel, for example together located in one and the same stripper or degassing tank.

According to one embodiment of the present invention, the first gas replacement region and the second gas replacement region are together located in one and the same vessel, and there exists at least one partition structural member between the first gas replacement region and the second gas replacement region. Herein, as the partition structural member, for example, a plate or ring-shaped partition structural member can be specifically enumerated.

According to one embodiment of the present invention, the central axis direction of the first gas replacement region is basically parallel with the central axis direction of the second gas replacement region.

According to one embodiment of the present invention, in a direction perpendicular to the horizontal plane, the inlet for the replacement gas of the first gas replacement region is substantially at the same level as or above the inlet for the replacement gas of the second gas replacement region or the bottom of the first gas replacement region is substantially at the same level as or above the bottom of the second gas replacement region.

According to one embodiment of the present invention, the gas replacement apparatus further comprises one or more gas replacement regions (referred to as additional gas replacement region(s)) before the first gas replacement region, after the first gas replacement region and before the second gas replacement region, and/or after the second gas replacement region. To this end, although the first gas replacement region and the second gas replacement region are communicated in the successive order, one or more additional gas replacement regions may sometimes be inserted between these two regions according to circumstances. Herein, as the additional gas replacement region, it can be any structural style of the gas replacement region known in the art, and it can either be identical to the first gas replacement region or identical to the second gas replacement region without particular limitation. Preferably, the first gas replacement region is directly communicated with the second gas replacement region. That is to say, no other gas replacement region is inserted between the first gas replacement region and the second gas replacement region, and the stream to be replaced is passed through the first gas replacement region and the second gas replacement region and the gas replacement is continuously performed.

According to one embodiment of the present invention, a flow disturbance structural member is provided in the first gas replacement region.

According to one embodiment of the present invention, a flow disturbance structural member is provided in the second gas replacement region.

According to one embodiment of the present invention, a flow disturbance structural member is provided in the additional gas replacement region.

According to one embodiment of the present invention, the flow disturbance structural member comprises at least one flow rectifier and a connecting piece for fixing said at least one flow rectifier relative to the corresponding gas replacement region and/or in relation to one another (when a plurality of the flow rectifiers are present). Herein, as the quantity of the flow rectifier, for example, 1-1000 or 4-100 can be enumerated, but not limited thereto in some cases.

According to one embodiment of the present invention, as the connecting piece, any structural style of the structural member used in the art for connecting or fixing the flow rectifier or the flow disturbance structural member can be directly applied without particular limitation, and for example, grid, screen mesh, metal strip, metal rod, metal wire and metal plate and others can be specifically enumerated.

According to one embodiment of the present invention, as the flow rectifier, for example, any structural style of flow rectifier that is used in the art for changing or leading the gas flow can be enumerated, but preferably, the flow rectifier is selected from at least one of a streamline flow rectifier, a diamond-shaped flow rectifier and an inclined baffle cross-flow type flow rectifier.

According to one embodiment of the present invention, the streamline flow rectifier is selected from at least one of a combination of two semiellipsoids, a combination of one semiellipsoid and one cone, a combination of one semiellipsoid and one circular arc streamlined body and a combination of one semiellipsoid and one paraboloid, preferably a combination of one semiellipsoid and one paraboloid. Herein, preferably, the generatrix of the paraboloid satisfies the curve equation $$y = \pm \frac{d}{2}\left(1 - \frac{x^2}{b^2}\right),$$

wherein d is the maximum cross section diameter (the unit is mm), b is the numerical value between 0.5-8.

According to one embodiment of the present invention, the diamond-shaped flow rectifier is selected from at least one of a combination of two pyramids, a combination of two prismoids, and a combination of one pyramid and one prismoid, preferably a combination of two pyramids.

According to one embodiment of the present invention, the inclined baffle cross-flow type flow rectifier is a plurality of baffles inclined with respect to a horizontal plane. Herein, as the angle of inclination with respect to a horizontal plane, it is generally 0-60°, preferably 10-40°.

According to one embodiment of the present invention, the central axis direction of said at least one flow rectifier substantially conforms to the central axis direction of the corresponding gas replacement region. In the context of the present invention, the so-called corresponding gas replacement region refers to the gas replacement region where the flow disturbance structural member or the flow rectifier is provided, for example the first gas replacement region or the second gas replacement region.

According to one embodiment of the present invention, at least one (for example each) flow rectifier has at least one run-through flow channel. Preferably, the ratio of the cross-sectional area of the run-through flow channel (in case that a plurality of said run-through flow channels are present, referring to the sum of the cross-sectional areas of the multiple run-through flow channels, the unit is m$^2$) to the maximum cross-sectional area of the corresponding flow rectifier (the unit is m$^2$) is 1-30:100 or 3-15:100. Herein, as the run-through flow channel, a through hole or a through slit is generally mentioned. In addition, the run-through flow channel may be arranged on the flow rectifier in any manner known in the art, but is preferably arranged along the central axis direction of the corresponding gas replacement region.

According to one embodiment of the present invention, in each flow disturbance structural member, the ratio of the maximum cross-sectional area of the flow rectifier (when a plurality of the flow rectifiers are present, referring to the sum of the maximum cross-sectional areas of the multiple flow rectifiers, the unit is m$^2$) to the corresponding cross-sectional area of the corresponding gas replacement region (the unit is m$^2$) is 20-90:100, preferably 45-65:100.

According to one embodiment of the present invention, in each flow disturbance structural member, when a plurality of the flow rectifiers are present, the multiple flow rectifiers in relation to one another are arranged in a predetermined manner. Here, as the arrangement manner, any manner conventionally known in the art can be cited, specifically, for example, the manner of random, triangle, square, rectangle, circle, or ring and the like can be cited.

According to one embodiment of the present invention, one or more flow disturbance structural members are arranged along the central axis direction of the corresponding gas replacement region.

Herein, as the number of the flow disturbance structural members, for example, 2-20 or 4-10 can be enumerated, but not limited thereto in some cases.

According to one embodiment of the present invention, when a plurality of the flow disturbance structural members are arranged along the central axis direction of the corresponding gas replacement region, the vertical distance (the unit is m) between any two adjacent flow disturbance structural members in relation to one another along the central axis direction of the corresponding gas replacement region can be 2% H-20% H. Herein, H is the height (the unit is m) of the corresponding gas replacement region.

According to one embodiment of the present invention, assuming the height (the unit is m) of the first gas replacement region is H1, assuming the height (the unit is m) of the second gas replacement region is H2, then H2/H1≥1 or 2≥H2/H1≥1.

According to one embodiment of the present invention, it also relates to a reaction system, especially a nitro compound hydrogenation reaction system. The reaction system comprises at least one reactor and at least one (for example 1-3 or 2) gas replacement apparatus communicated with (for example communicated downstream with) said at least one reactor. Herein, the gas replacement apparatus is generally configured to receive an effluent from said at least one reactor especially configured to receive the spent catalyst particles from said at least one reactor. In addition, at least one of the gas replacement apparatuses is configured to implement the gas replacement apparatus of the gas replacement process according to any of the above-mentioned embodiments of the present invention or is the gas replacement apparatus according to any of the above-mentioned embodiments of the present invention.

According to one embodiment of the present invention, as the reactor, it is preferably a fluidized bed reactor, especially a reactor having a fluidized bed of catalyst particles, more especially a fluidized bed reactor for the nitro compound hydrogenation, and more especially a fluidized bed reactor for producing aniline by the hydrogenation of nitrobenzene.

According to one embodiment of the present invention, the spent catalyst particles are subjected to the gas replacement (especially degassing) in said at least one gas replacement apparatus, and then further regenerated/activated, and then recycled back to said at least one reactor.

According to one embodiment of the present invention, it also relates to a nitro compound hydrogenation reaction process. Preferably, the nitro compound hydrogenation reaction process is carried out in the nitro compound hydrogenation reaction system according to any of the previous embodiments of the present invention.

According to one embodiment of the present invention, the nitro compound hydrogenation reaction process at least comprises a step of contacting a nitro compound and hydrogen gas as the reaction raw material with a hydrogenation catalyst to obtain a reaction product and a spent catalyst (referred to as a hydrogenation reaction step) and a step of subjecting the spent catalyst to the gas replacement in the presence of a replacement gas (referred to as the gas replacement step).

According to one embodiment of the present invention, the gas replacement step is performed according to the gas replacement process mentioned in any of the previous embodiments of the present invention, or performed in the gas replacement apparatus according to any of the previous embodiments of the present invention.

According to one embodiment of the present invention, the spent catalyst particles are subjected to the gas replacement in the gas replacement step, then further regenerated/activated, and then recycled back to the hydrogenation reaction step.

With reference to FIG. 1, the nitro compound hydrogenation reaction system or the hydrogenation reaction process will be specifically described. Specifically, the main equipments of the nitro compound hydrogenation reaction system or the hydrogenation reaction process comprise: a fluidized bed reactor 3, a degassing tank for the spent catalyst 12, a regenerator 13, a degassing tank for the catalyst to be activated 16, an activator 19 and a lifting pipe 21, wherein in the fluidized bed reactor 3 are included a dense phase reaction zone 4 located in the lower section, a particle sputtering transition zone 5 located in the middle section and a dilute-phase zone 7 located in the upper section, the degassing tank for the spent catalyst 12 is communicated with the fluidized bed reactor 3 and the regenerator 13 respectively, the degassing tank for the catalyst to be activated 16 is communicated with the regenerator 13 and the activator 19 respectively, the lifting pipe 21 is communicated with the activator 19 and the fluidized bed reactor 3 respectively. In the fluidized bed reactor 3 are provided a gas distributor 2, a heat-exchanging pipe 11 and a cyclone separator 9. Herein, the degassing tank for the spent catalyst 12 comprises a degassing descending countercurrent zone (corresponding to the first gas replacement region or the first gas replacement step of the present invention) and a degassing ascending co-current zone (corresponding to the second gas replacement region or the second gas replacement step of the present invention), and in the degassing descending countercurrent zone and the degassing ascending co-current zone are respectively provided flow disturbance structural members 33; the degassing tank for the catalyst to be activated 16 comprises a regeneration degassing descending countercurrent zone (corresponding to the first gas replacement region or the first gas replacement step of the present invention) and a regeneration degassing ascending co-current zone (corresponding to the second gas replacement region or the second gas replacement step of the present invention), and in the regeneration degassing descending countercurrent zone and the regeneration degassing ascending co-current zone are respectively provided flow disturbance structural members 33. The degassing tank for the spent catalyst 12 and the degassing tank for the catalyst to be activated 16 are the gas replacement apparatus of the present invention or the gas replacement process of the present invention is implemented therein.

According to one embodiment of the present invention, in the nitro compound hydrogenation reaction system or the hydrogenation reaction process, vaporized nitrobenzene and hydrogen gas as raw material are introduced into a gas chamber, then into the fluidized bed reactor 3 through the gas distributor 2 to push the catalyst in the reactor to be fluidized, then react in the dense phase reaction zone 4 to produce an aniline product, a part of the gas phase forms bubbles, the particle sputtering occurs at the top of the dense phase reaction zone 4 to form a particle sputtering transition zone 5, the particles enter the dilute-phase zone 7 to be separated with a cyclone separator 9 and return to the dense phase reaction zone 4, the crude product gas 8 flows out of the fluidized bed reactor 3 and is sent into the subsequent separation section. After the catalyst is partly coked in the reaction, the coked catalyst is degassed in the degassing tank for the spent catalyst 12, and introduced into the regenerator 13, to which the oxygen is introduced, the catalyst is regenerated by carbon burning.< The regenerated catalyst is then introduced into the degassing tank for the catalyst to be activated 16 and degassed, and then introduced into the activator 19, to which hydrogen gas is introduced, the catalyst is activated, and the activated catalyst is introduced into the lifting pipe 21, and lifted up to return to the fluidized bed reactor 3 to proceed with the catalysis.

According to one embodiment of the present invention, in the hydrogenation reaction step or the fluidized bed reactor 3, the gas superficial velocity is generally 0.2-0.8 m/s, the molar ratio of hydrogen gas to the reaction raw material (for example nitrobenzene) is generally 6-21.

According to one embodiment of the present invention, in the hydrogenation reaction step or the fluidized bed reactor 3, the reaction temperature (generally referring to the average reaction temperature in the dense phase reaction zone) is 220-280° C., the reaction pressure (generally referring to the pressure in the dense phase reaction zone) is 0.05-1 MPa (gauge pressure). In addition, the temperature in the vicinity of the gas distributor is generally controlled at 320° C. or less.

According to one embodiment of the present invention, the reaction conditions in the regenerator 13 comprise: the gas superficial velocity is 0.1-0.6 m/s, and the average regeneration temperature is 350-450° C.; the reaction conditions in the activator 19 comprise: the gas superficial velocity is 0.1-0.6 m/s, and the average activation temperature is 200-250° C.

According to one embodiment of the present invention, the ratio of the gas superficial velocity of the degassing descending countercurrent zone to the gas superficial velocity of the degassing ascending co-current zone in the degassing tank for the spent catalyst 12 is 1/15-1, the degassing agent is one or more (as mixture) of nitrogen gas, water vapor, carbon dioxide, methane, and argon gas, the gas component carried over from the fluidized bed reactor 3 is replaced out. The ratio of the gas superficial velocity of regeneration degassing descending countercurrent zone to the gas superficial velocity of regeneration degassing ascending co-current zone in the degassing tank for the catalyst to be activated 16 is 1/15-1, the degassing agent is one or more (as mixture) of nitrogen gas, water vapor, carbon dioxide, oxygen gas, and argon gas, the oxygen-containing gas component carried over from the regenerator 13 is replaced out.

According to one embodiment of the present invention, the degassing efficiency of the degassing tank for the spent catalyst and the degassing tank for the catalyst to be activated can generally reach 90% or higher, preferably 94% or higher. In addition, these degassing tanks in two regions have a large contact area and a high level of mass transfer and heat transfer, and the degassing efficiency meets the requirements of production safety.

According to one embodiment of the present invention, as the hydrogenation catalyst, any catalyst used in the art for the hydrogenation reaction of the nitro compound can be enumerated, and at least one selected from a copper-based loaded catalyst, a nickel-based loaded catalyst and a noble metal-based loaded catalyst, more especially a copper-based loaded catalyst can be particularly enumerated. Herein, for the copper-based loaded catalyst, copper is generally used as the main active component, and the support is generally alumina or silica.

According to one embodiment of the present invention, the average particle diameter of the hydrogenation catalyst is generally 30-800 μm, preferably 40-500 μm or 50-600 μm. Preferably, in the hydrogenation catalyst, the catalyst particles having a particle diameter of less than 80 μm comprises not less than 2 wt %, preferably 5-15 wt % by mass percent of all catalyst particles. For example, the particle average diameter can be obtained by the analysis of the sampled solid catalyst particles with a particle-size analyzer.

According to one embodiment of the present invention, the replacement gas is generally gas or vapor or steam. Herein, as the replacement gas, at least one selected from nitrogen gas, water vapor, carbon dioxide, methane, oxygen gas and argon gas can be particularly enumerated, especially nitrogen gas. Those skilled in the art can proceed the conventional selection according to the actual requirements without particular limitation.

According to an embodiment of the present invention, the nitro compound is selected from at least one of the compounds represented by the following formula (1), especially nitrobenzene.

$$R-NO_2 \tag{1}$$

According to an embodiment of the present invention, in the structural formula (1), R is an optionally substituted $C_{2-20}$ straight, branched or cyclic hydrocarbyl, preferably an optionally substituted $C_{4-20}$ cyclic hydrocarbyl, especially an optionally substituted $C_{6-20}$ aryl, more especially an optionally substituted phenyl or phenyl.

EXAMPLES

The present invention will be described in further detail below by way of examples and comparative examples, but the present invention is not limited to the following examples.

In the following examples and comparative examples, the carbon deposition amount was measured and analyzed with thermogravimetric analyzer.

Example 1

Figure 2:
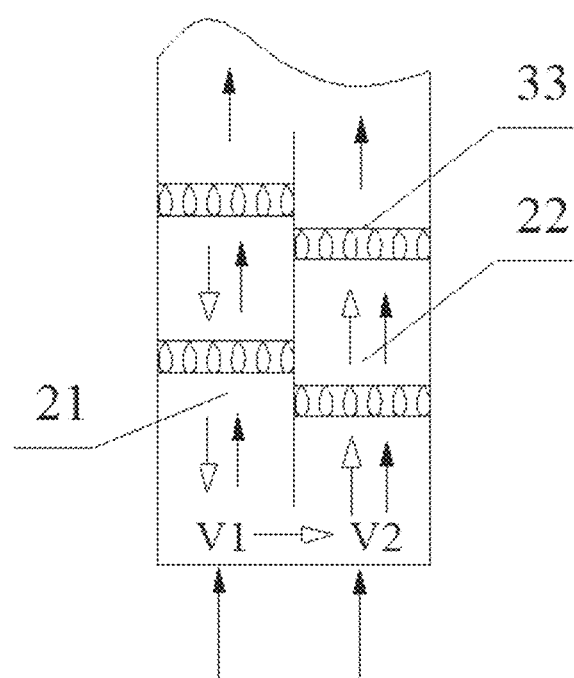
FIG. 2 is a schematic flow diagram for an embodiment of the gas replacement process (especially a degassing process) of the present invention.

The reaction system for producing aniline by the hydrogenation of nitrobenzene as shown in FIG. 1 was used. The degassing tank for the spent catalyst and the degassing tank for the catalyst to be activated were degassed according to the degassing process as shown in FIG. 2. The flow rectifier of the flow disturbance structural member was a streamline flow rectifier.

The catalyst was a metal loaded catalyst with copper as the main active component, the support was silica, the catalyst had an average particle diameter of 400 μm, and the content of particles lower than 80 μm was 6%. The reaction conditions in the fluidized bed reactor were as follows: the gas superficial velocity was 0.4 m/s, the molar ratio of hydrogen gas to nitrobenzene was 11, the average reaction temperature in the dense phase reaction zone was controlled at 240° C., and the reaction pressure in the dense phase reaction zone was 0.1 MPa. The reaction conditions in the regenerator were as follows: the gas superficial velocity was 0.3 m/s, and the average regeneration temperature was 410° C.; and the reaction conditions in the activator were as follows: the gas superficial velocity was 0.3 m/s, and the average activation temperature was 220° C. The ratio of the superficial velocity of the first gas replacement step to the superficial velocity of the second gas replacement step in the degassing tank for the spent catalyst was 1/5, the degassing agent was nitrogen gas; the ratio of the superficial velocity of the first gas replacement step to the superficial velocity of the second gas replacement step in the degassing tank for the catalyst to be activated was 1/5, the degassing agent was nitrogen gas. In the first gas replacement steps for the degassing tank for the spent catalyst and for the degassing tank for the catalyst to be activated, the average solid content rates were both 0.55; in the second gas replacement steps for the degassing tank for the spent catalyst and for the degassing tank for the catalyst to be activated, the average solid content rates were both 0.12. In this Example, V1=0.25 m/s, V2=1.25 m/s.

The degassing efficiencies for the degassing tank for the spent catalyst and the degassing tank for the catalyst to be activated were both 98.7%, the carbon deposition amount when the reaction time was 90 minutes under the high space velocity condition (0.9 h$^{-1}$) could be controlled at not greater than 0.5%, and the results were detailed in Table 1.

Example 2

The reaction system for producing aniline by the hydrogenation of nitrobenzene as shown in FIG. 1 was used. The degassing tank for the spent catalyst and the degassing tank for the catalyst to be activated were degassed according to the degassing process as shown in FIG. 2. The flow rectifier of the flow disturbance structural member is a diamond-shaped flow rectifier.

The catalyst was a metal loaded catalyst with copper as the main active component, the support was silica, the catalyst had an average particle diameter of 400 μm, and the content of particles lower than 80 μm was 6%. The reaction conditions in the fluidized bed reactor were as follows: the gas superficial velocity was 0.4 m/s, the molar ratio of hydrogen gas to nitrobenzene was 11, the average reaction temperature in the dense phase reaction zone was controlled at 240° C., and the reaction pressure in the dense phase reaction zone was 0.1 MPa. The reaction conditions in the regenerator were as follows: the gas superficial velocity was 0.3 m/s, and the average regeneration temperature was 410° C.; and the reaction conditions in the activator were as follows: the gas superficial velocity was 0.3 m/s, and the average activation temperature was 220° C. The ratio of the superficial velocity of the first gas replacement step to the superficial velocity of the second gas replacement step in the degassing tank for the spent catalyst was 1/5, the degassing agent was nitrogen gas; the ratio of the superficial velocity of the first gas replacement step to the superficial velocity of the second gas replacement step in the degassing tank for the catalyst to be activated was 1/5, the degassing agent was nitrogen gas. In the first gas replacement steps for the degassing tank for the spent catalyst and for the degassing tank for the catalyst to be activated, the average solid content rates were both 0.55; in the second gas replacement steps for the degassing tank for the spent catalyst and for the degassing tank for the catalyst to be activated, the average solid content rates were both 0.12.

The degassing efficiencies for the degassing tank for the spent catalyst and the degassing tank for the catalyst to be activated were both 97.3%, the carbon deposition amount when the reaction time was 90 minutes under the high space velocity condition (0.9 h$^{-1}$) could be controlled at not greater than 0.5%, and the results were detailed in Table 1.

Example 3

The reaction system for producing aniline by the hydrogenation of nitrobenzene as shown in FIG. 1 was used. The degassing tank for the spent catalyst and the degassing tank for the catalyst to be activated were degassed according to the degassing process as shown in FIG. 2. The flow rectifier of the flow disturbance structural member was an inclined baffle cross-flow type flow rectifier.

The catalyst was a metal loaded catalyst with copper as the main active component, the support was silica, the catalyst had an average particle diameter of 400 μm, and the content of particles lower than 80 μm was 6%. The reaction conditions in the fluidized bed reactor were as follows: the gas superficial velocity was 0.4 m/s, the molar ratio of hydrogen gas to nitrobenzene was 11, the average reaction temperature in the dense phase reaction zone was controlled at 240° C., and the reaction pressure in the dense phase reaction zone was 0.1 MPa. The reaction conditions in the regenerator were as follows: the gas superficial velocity was 0.3 m/s, and the average regeneration temperature was 410° C.; and the reaction conditions in the activator were as follows: the gas superficial velocity was 0.3 m/s, and the average activation temperature was 220° C. The ratio of the superficial velocity of the first gas replacement step to the superficial velocity of the second gas replacement step in the degassing tank for the spent catalyst was 1/5, the degassing agent was nitrogen gas; the ratio of the superficial velocity of the first gas replacement step in the degassing tank for the catalyst to be activated to the superficial velocity of the second gas replacement step in the degassing tank for the catalyst to be activated was 1/5, the degassing agent was nitrogen gas. In the first gas replacement steps for the degassing tank for the spent catalyst and for the degassing tank for the catalyst to be activated, the average solid content rates were both 0.55; in the second gas replacement steps for the degassing tank for the spent catalyst and for the degassing tank for the catalyst to be activated, the average solid content rates were both 0.12.

The degassing efficiencies for the degassing tank for the spent catalyst and the degassing tank for the catalyst to be activated were both 97.1%, the carbon deposition amount when the reaction time was 90 minutes under the high space velocity condition (0.9 h$^{-1}$) could be controlled at no greater than 0.5%, and the results were detailed in Table 1.

Example 4

The reaction system for producing aniline by the hydrogenation of nitrobenzene as shown in FIG. 1 was used. The degassing tank for the spent catalyst and the degassing tank for the catalyst to be activated were degassed according to the degassing process as shown in FIG. 2. The flow rectifier of the flow disturbance structural member was a streamline flow rectifier.

The catalyst was a metal loaded catalyst with copper as the main active component, the support was silica, the catalyst had an average particle diameter of 400 μm, and the content of particles lower than 80 μm was 6%. The reaction conditions in the fluidized bed reactor were as follows: the gas superficial velocity was 0.4 m/s, the molar ratio of hydrogen gas to nitrobenzene was 11, the average reaction temperature in the dense phase reaction zone was controlled at 240° C., and the reaction pressure in the dense phase reaction zone was 0.1 MPa. The reaction conditions in the regenerator were as follows: the gas superficial velocity was 0.1 m/s, and the average regeneration temperature was 410° C.; the reaction conditions in the activator were as follows: the gas superficial velocity was 0.3 m/s, and the average activation temperature was 220° C. The ratio of the superficial velocity of the first gas replacement step to the superficial velocity of the second gas replacement step in the degassing tank for the spent catalyst was 1/5, the degassing agent was nitrogen gas; the ratio of the superficial velocity of the first gas replacement step to the superficial velocity of the second gas replacement step in the degassing tank for the catalyst to be activated was 1/5, the degassing agent was nitrogen gas. In the first gas replacement steps for the degassing tank for the spent catalyst and for the degassing tank for the catalyst to be activated, the average solid content rates were both 0.55; in the second gas replacement steps for the degassing tank for the spent catalyst and for the degassing tank for the catalyst to be activated, the average solid content rates were both 0.12.

The degassing efficiencies for the degassing tank for the spent catalyst and the degassing tank for the catalyst to be activated were both 98.7%, the carbon deposition amount when the reaction time was 90 minutes under the high space velocity condition (0.9 h$^{-1}$) could be controlled at no greater than 0.7%, and the results were detailed in Table 1.

Example 5

The reaction system for producing aniline by the hydrogenation of nitrobenzene as shown in FIG. 1 was used. The degassing tank for the spent catalyst and the degassing tank for the catalyst to be activated were degassed according to the degassing process as shown in FIG. 2. The flow rectifier of the flow disturbance structural member was a streamline flow rectifier.

The catalyst was a metal loaded catalyst with copper as the main active component, the support was silica, the catalyst had an average particle diameter of 400 μm, and the content of particles lower than 80 μm was 6%. The reaction conditions in the fluidized bed reactor were as follows: the gas superficial velocity was 0.6 m/s, the molar ratio of hydrogen gas to nitrobenzene was 11, the average reaction temperature in the dense phase reaction zone was controlled at 240° C., and the reaction pressure in the dense phase reaction zone was 0.1 MPa. The reaction conditions in the regenerator were as follows: the gas superficial velocity was 0.3 m/s, and the average regeneration temperature was 410° C.; and the reaction conditions in the activator were as follows: the gas superficial velocity was 0.3 m/s, and the average activation temperature was 220° C. The ratio of the superficial velocity of the first gas replacement step to the superficial velocity of the second gas replacement step in the degassing tank for the spent catalyst was 1/5, the degassing agent was nitrogen gas; the ratio of the superficial velocity of the first gas replacement step to the superficial velocity of the second gas replacement step in the degassing tank for the catalyst to be activated was 1/5, the degassing agent was nitrogen gas. In the first gas replacement steps for the degassing tank for the spent catalyst and for the degassing tank for the catalyst to be activated, the average solid content rates were both 0.55; in the second gas replacement steps for the degassing tank for the spent catalyst and for the degassing tank for the catalyst to be activated, the average solid content rates were both 0.12.

The degassing efficiencies for the degassing tank for the spent catalyst and the degassing tank for the catalyst to be activated were both 98.7%, the carbon deposition amount when the reaction time was 90 minutes under the high space velocity condition (0.9 h$^{-1}$) could be controlled at no greater than 0.3%, and the results were detailed in Table 1.

Example 6

The reaction system for producing aniline by the hydrogenation of nitrobenzene as shown in FIG. 1 was used. The degassing tank for the spent catalyst and the degassing tank for the catalyst to be activated were degassed according to the degassing process as shown in FIG. 2. The flow rectifier of the flow disturbance structural member was a streamline flow rectifier.

The catalyst was a metal loaded catalyst with copper as the main active component, the support was silica, the catalyst had an average particle diameter of 400 μm, and the content of particles lower than 80 μm was 6%. The reaction conditions in the fluidized bed reactor were as follows: the gas superficial velocity was 0.4 m/s, the molar ratio of hydrogen gas to nitrobenzene was 11, the average reaction temperature in the dense phase reaction zone was controlled at 240° C., and the reaction pressure in the dense phase reaction zone was 0.1 MPa. The reaction conditions in the regenerator were as follows: the gas superficial velocity was 0.3 m/s, and the average regeneration temperature was 350° C.; the reaction conditions in the activator were as follows: the gas superficial velocity was 0.3 m/s, and the average activation temperature was 220° C. The ratio of the superficial velocity of the first gas replacement step to the superficial velocity of the second gas replacement step in the degassing tank for the spent catalyst was 1/5, the degassing agent was nitrogen gas; the ratio of the superficial velocity of the first gas replacement step to the superficial velocity of the second gas replacement step in the degassing tank for the catalyst to be activated was 1/5, the degassing agent was nitrogen gas. In the first gas replacement steps for the degassing tank for the spent catalyst and for the degassing tank for the catalyst to be activated, the average solid content rates were both 0.55; in the second gas replacement steps for the degassing tank for the spent catalyst and for the degassing tank for the catalyst to be activated, the average solid content rates were both 0.12.

The degassing efficiencies for the degassing tank for the spent catalyst and the degassing tank for the catalyst to be activated were both 98.7%, the carbon deposition amount when the reaction time was 90 minutes under the high space velocity condition (0.9 h$^{-1}$) could be controlled at no greater than 1%, and the results were detailed in Table 2.

Example 7

The reaction system for producing aniline by the hydrogenation of nitrobenzene as shown in FIG. 1 was used. The degassing tank for the spent catalyst and the degassing tank for the catalyst to be activated were degassed according to the degassing process as shown in FIG. 2. The flow rectifier of the flow disturbance structural member was a streamline flow rectifier.

The catalyst was a metal loaded catalyst with copper as the main active component, the support was silica, the catalyst had an average particle diameter of 400 μm, and the content of particles lower than 80 μm was 6%. The reaction conditions in the fluidized bed reactor were as follows: the gas superficial velocity was 0.4 m/s, the molar ratio of hydrogen gas to nitrobenzene was 11, the average reaction temperature in the dense phase reaction zone was controlled at 240° C., and the reaction pressure in the dense phase reaction zone was 0.1 MPa. The reaction conditions in the regenerator were as follows: the gas superficial velocity was 0.3 m/s, and the average regeneration temperature was 450° C.; the reaction conditions in the activator were as follows: the gas superficial velocity was 0.3 m/s, and the average activation temperature was 220° C. The ratio of the superficial velocity of the first gas replacement step to the superficial velocity of the second gas replacement step in the degassing tank for the spent catalyst was 1/5, the degassing agent was nitrogen gas; the ratio of the superficial velocity of the first gas replacement step to the superficial velocity of the second gas replacement step in the degassing tank for the catalyst to be activated was 1/5, the degassing agent was nitrogen gas. In the first gas replacement steps for the degassing tank for the spent catalyst and for the degassing tank for the catalyst to be activated, the average solid content rates were both 0.55; in the second gas replacement steps for the degassing tank for the spent catalyst and for the degassing tank for the catalyst to be activated, the average solid content rates were both 0.12.

The degassing efficiencies for the degassing tank for the spent catalyst and the degassing tank for the catalyst to be activated were both 98.7%, the carbon deposition amount when the reaction time was 90 minutes under the high space velocity condition (0.9 h$^{-1}$) could be controlled at no greater than 0.15%, and the results were detailed in Table 2.

Example 8

The reaction system for producing aniline by the hydrogenation of nitrobenzene as shown in FIG. 1 was used. The degassing tank for the spent catalyst and the degassing tank for the catalyst to be activated were degassed according to the degassing process as shown in FIG. 2. The flow rectifier of the flow disturbance structural member was a streamline flow rectifier.

The catalyst was a metal loaded catalyst with copper as the main active component, the support was silica, the catalyst had an average particle diameter of 400 μm, and the content of particles lower than 80 μm was 6%. The reaction conditions in the fluidized bed reactor were as follows: the gas superficial velocity was 0.4 m/s, the molar ratio of hydrogen gas to nitrobenzene was 11, the average reaction temperature in the dense phase reaction zone was controlled at 240° C., and the reaction pressure in the dense phase reaction zone was 0.1 MPa. The reaction conditions in the regenerator were as follows: the gas superficial velocity was 0.3 m/s, and the average regeneration temperature was 410° C.; and the reaction conditions in the activator were as follows: the gas superficial velocity was 0.3 m/s, and the average activation temperature was 220° C. The ratio of the superficial velocity of the first gas replacement step to the superficial velocity of the second gas replacement step in the degassing tank for the spent catalyst was 1/15, the degassing agent was nitrogen gas; the ratio of the superficial velocity of the first gas replacement step to the superficial velocity of the second gas replacement step in the degassing tank for the catalyst to be activated was 1/15, the degassing agent was nitrogen gas. In the first gas replacement steps for the degassing tank for the spent catalyst and for the degassing tank for the catalyst to be activated, the average solid content rates were both 0.59; in the second gas replacement steps for the degassing tank for the spent catalyst and for the degassing tank for the catalyst to be activated, the average solid content rates were both 0.065.

The degassing efficiencies for the degassing tank for the spent catalyst and the degassing tank for the catalyst to be activated were both 98.2%, the carbon deposition amount when the reaction time was 90 minutes under the high space velocity condition (0.9 h$^{-1}$) could be controlled at no greater than 0.5%, and the results were detailed in Table 2.

Example 9

The reaction system for producing aniline by the hydrogenation of nitrobenzene as shown in FIG. 1 was used. The degassing tank for the spent catalyst and the degassing tank for the catalyst to be activated were degassed according to the degassing process as shown in FIG. 2. The flow rectifier of the flow disturbance structural member was a streamline flow rectifier.

The catalyst was a metal loaded catalyst with copper as the main active component, the support was silica, the catalyst had an average particle diameter of 400 μm, and the content of particles lower than 80 μm was 6%. The reaction conditions in the fluidized bed reactor were as follows: the gas superficial velocity was 0.4 m/s, the molar ratio of hydrogen gas to nitrobenzene was 11, the average reaction temperature in the dense phase reaction zone was controlled at 240° C., and the reaction pressure in the dense phase reaction zone was 0.1 MPa. The reaction conditions in the regenerator were as follows: the gas superficial velocity was 0.3 m/s, and the average regeneration temperature was 410° C.; and the reaction conditions in the activator were as follows: the gas superficial velocity was 0.3 m/s, and the average activation temperature was 220° C. The ratio of the superficial velocity of the first gas replacement step to the superficial velocity of the second gas replacement step in the degassing tank for the spent catalyst was 1/2, the degassing agent was nitrogen gas; the ratio of the superficial velocity of the first gas replacement step to the superficial velocity of the second gas replacement step in the degassing tank for the catalyst to be activated was 1/2, the degassing agent was nitrogen gas. In the first gas replacement steps for the degassing tank for the spent catalyst and for the degassing tank for the catalyst to be activated, the average solid content rates were both 0.46; in the second gas replacement steps for the degassing tank for the spent catalyst and for the degassing tank for the catalyst to be activated, the average solid content rates were both 0.18.

The degassing efficiencies for the degassing tank for the spent catalyst and the degassing tank for the catalyst to be activated were both 96.8%, the carbon deposition amount when the reaction time was 90 minutes under the high space velocity condition (0.9 h$^{-1}$) could be controlled at no greater than 0.5%, and the results were detailed in Table 2.

Example 10

The reaction system for producing aniline by the hydrogenation of nitrobenzene as shown in FIG. 1 was used. The degassing tank for the spent catalyst and the degassing tank for the catalyst to be activated were degassed according to the degassing process as shown in FIG. 2. The flow rectifier of the flow disturbance structural member was a streamline flow rectifier.

The catalyst was a metal loaded catalyst with copper as the main active component, the support was silica, the catalyst had an average particle diameter of 400 μm, and the content of particles lower than 80 μm was 6%. The reaction conditions in the fluidized bed reactor were as follows: the gas superficial velocity was 0.4 m/s, the molar ratio of hydrogen gas to nitrobenzene was 11, the average reaction temperature in the dense phase reaction zone was controlled at 240° C., and the reaction pressure in the dense phase reaction zone was 0.1 MPa. The reaction conditions in the regenerator were as follows: the gas superficial velocity was 0.3 m/s, and the average regeneration temperature was 410° C.; and the reaction conditions in the activator were as follows: the gas superficial velocity was 0.3 m/s, and the average activation temperature was 220° C. The ratio of the superficial velocity of the first gas replacement step to the superficial velocity of the second gas replacement step in the degassing tank for the spent catalyst was 1/20, the degassing agent was nitrogen gas; the ratio of the superficial velocity of the first gas replacement step to the superficial velocity of the second gas replacement step in the degassing tank for the catalyst to be activated was 1/20, the degassing agent was nitrogen gas. In the first gas replacement steps for the degassing tank for the spent catalyst and for the degassing tank for the catalyst to be activated, the average solid content rates were both 0.61; in the second gas replacement steps for the degassing tank for the spent catalyst and for the degassing tank for the catalyst to be activated, the average solid content rates were both 0.058.

The degassing efficiencies for the degassing tank for the spent catalyst and the degassing tank for the catalyst to be activated were both 98.9%, the carbon deposition amount when the reaction time was 90 minutes under the high space velocity condition ($0.9\ h^{-1}$) could be controlled at no greater than 0.5%, and the results were detailed in Table 2.

Example 11

Figure 3:
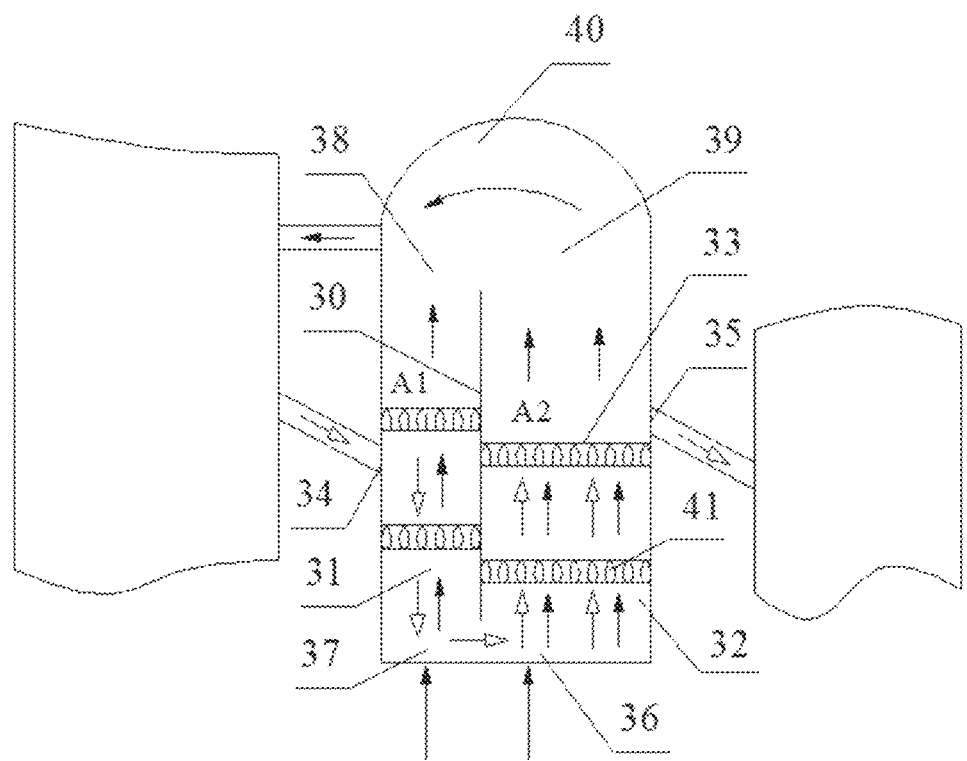
FIG. 3 is a schematic flow diagram for an embodiment of the gas replacement apparatus (especially the degassing tank for the spent catalyst or the degassing tank for the catalyst to be activated) of the present invention.
Figure 4:
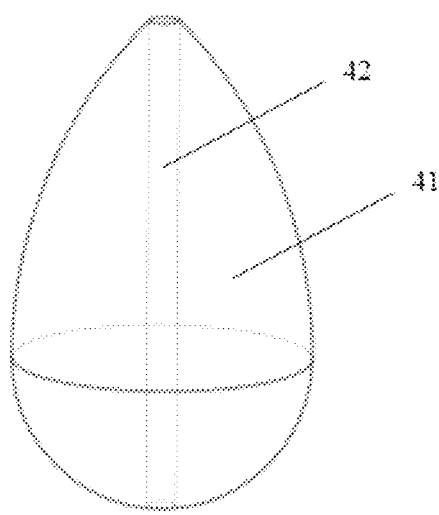
FIG. 4 is a schematic diagram for an embodiment of the streamline flow rectifier of the present invention, wherein 42 represents the run-through flow channel.
Figure 5:
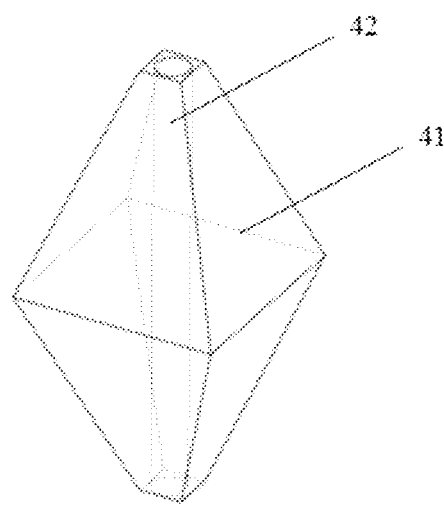
FIG. 5 is a schematic diagram for an embodiment of the diamond-shaped flow rectifier of the present invention, wherein 42 represents the run-through flow channel.
Figure 6:
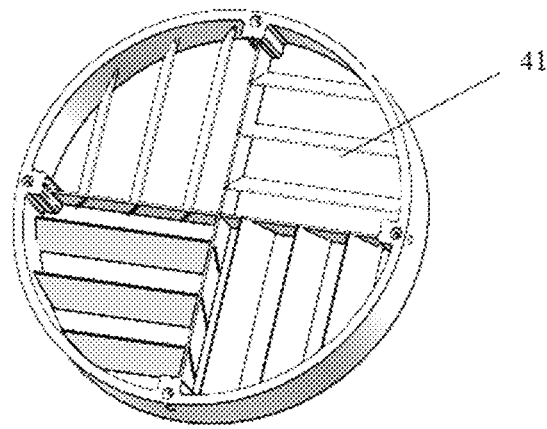
FIG. 6 is a schematic diagram for an embodiment of the inclined baffle cross-flow type flow rectifier of the present invention.

The reaction system for producing aniline by the hydrogenation of nitrobenzene as shown in FIG. 1 was used. The gas replacement apparatus as shown in FIG. 3 was used as the degassing tank for the spent catalyst and the degassing tank for the catalyst to be activated. The degassing tank for the spent catalyst and the degassing tank for the catalyst to be activated were degassed according to the degassing process as shown in FIG. 2.

In the degassing tank for the spent catalyst and the degassing tank for the catalyst to be activated, the ratio of the cross-sectional area of the middle part of the second gas replacement region to the cross-sectional area of the middle part of the first gas replacement region was 7, the number of the flow rectifier(s) contained by any flow disturbance structural member in the first gas replacement region was 4, the number of the flow rectifier(s) contained by any flow disturbance structural member in the second gas replacement region was 20, the flow rectifier was a streamline flow rectifier, the ratio of the cross-sectional area of the run-through flow channel to the maximum cross-sectional area of the corresponding flow rectifier was 10:100, the ratio of the sum of the maximum cross-sectional areas of the multiple flow rectifiers to the corresponding cross-sectional area of the corresponding gas replacement region was 50:100, the number of the flow disturbance structural member(s) disposed in the first gas replacement region was 2, the number of the flow disturbance structural member(s) disposed in the second gas replacement region was 2, the ratio of the vertical distance of any two flow disturbance structural members in relation to one another to (the height of) the corresponding gas replacement region was 0.5, the ratio of the height of the second gas replacement region to the height of the first gas replacement region was 1.5.

The catalyst was a metal loaded catalyst with copper as the main active component, the support was silica, the catalyst had an average particle diameter of 400 μm, and the content of particles lower than 80 μm was 6%. The reaction conditions in the fluidized bed reactor were as follows: the gas superficial velocity was 0.4 m/s, the molar ratio of hydrogen gas to nitrobenzene was 11, the average reaction temperature in the dense phase reaction zone was controlled at 240° C., and the reaction pressure in the dense phase reaction zone was 0.1 MPa. The reaction conditions in the regenerator were as follows: the gas superficial velocity was 0.3 m/s, and the average regeneration temperature was 410° C.; and the reaction conditions in the activator were as follows: the gas superficial velocity was 0.3 m/s, and the average activation temperature was 220° C. The ratio of the superficial velocity of the first gas replacement step to the superficial velocity of the second gas replacement step in the degassing tank for the spent catalyst was 1/5, the degassing agent was nitrogen gas; the ratio of the superficial velocity of the first gas replacement step to the superficial velocity of the second gas replacement step in the degassing tank for the catalyst to be activated was 1/5, the degassing agent was nitrogen gas. In the first gas replacement steps for the degassing tank for the spent catalyst and for the degassing tank for the catalyst to be activated, the average solid content rates were both 0.55; in the second gas replacement steps for the degassing tank for the spent catalyst and for the degassing tank for the catalyst to be activated, the average solid content rates were both 0.12.

The degassing efficiencies for the degassing tank for the spent catalyst and the degassing tank for the catalyst to be activated were both 98.8%, the carbon deposition amount when the reaction time was 90 minutes under the high space velocity condition ($0.9\ h^{-1}$) could be controlled at no greater than 0.5%, and the results were detailed in Table 3.

Example 12

The reaction system for producing aniline by the hydrogenation of nitrobenzene as shown in FIG. 1 was used. The gas replacement apparatus as shown in FIG. 3 was used as the degassing tank for the spent catalyst and the degassing tank for the catalyst to be activated. The degassing tank for the spent catalyst and the degassing tank for the catalyst to be activated were degassed according to the degassing process as shown in FIG. 2.

In the degassing tank for the spent catalyst and the degassing tank for the catalyst to be activated, the ratio of the cross-sectional area of the middle part of the second gas replacement region to the cross-sectional area of the middle part of the first gas replacement region was 1.5, the number of the flow rectifier(s) contained by any flow disturbance structural member in the first gas replacement region was 4, the number of the flow rectifier(s) contained by any flow disturbance structural member in the second gas replacement region was 20, the flow rectifier was a streamline flow rectifier, the ratio of the cross-sectional area of the run-through flow channel to the maximum cross-sectional area of the corresponding flow rectifier was 10:100, the ratio of the sum of the maximum cross-sectional areas of the multiple flow rectifiers to the corresponding cross-sectional area of the corresponding gas replacement region was 50:100, the number of the flow disturbance structural member(s) disposed in the first gas replacement region was 2, the number of the flow disturbance structural member(s) disposed in the second gas replacement region was 2, the ratio of the vertical distance of any two flow disturbance structural members in relation to one another to (the height of) the corresponding gas replacement region was 0.5, the ratio of the height of the second gas replacement region to the height of the first gas replacement region was 1.5.

The catalyst was a metal loaded catalyst with copper as the main active component, the support was silica, the catalyst had an average particle diameter of 400 μm, and the content of particles lower than 80 μm was 6%. The reaction conditions in the fluidized bed reactor were as follows: the gas superficial velocity was 0.4 m/s, the molar ratio of hydrogen gas to nitrobenzene was 11, the average reaction temperature in the dense phase reaction zone was controlled at 240° C., and the reaction pressure in the dense phase reaction zone was 0.1 MPa. The reaction conditions in the regenerator were as follows: the gas superficial velocity was 0.3 m/s, and the average regeneration temperature was 410° C.; and the reaction conditions in the activator were as follows: the gas superficial velocity was 0.3 m/s, and the average activation temperature was 220° C. The ratio of the superficial velocity of the first gas replacement step to the superficial velocity of the second gas replacement step in the degassing tank for the spent catalyst was 1/5, the degassing agent was nitrogen gas; the ratio of the superficial velocity of the first gas replacement step to the superficial velocity of the second gas replacement step in the degassing tank for the catalyst to be activated was 1/5, the degassing agent was nitrogen gas. In the first gas replacement steps for the degassing tank for the spent catalyst and for the degassing tank for the catalyst to be activated, the average solid content rates were both 0.55; in the second gas replacement steps for the degassing tank for the spent catalyst and for the degassing tank for the catalyst to be activated, the average solid content rates were both 0.12.

The degassing efficiencies for the degassing tank for the spent catalyst and the degassing tank for the catalyst to be activated were both 96.7%, the carbon deposition amount when the reaction time was 90 minutes under the high space velocity condition (0.9 h$^{-1}$) could be controlled at no greater than 0.5%, and the results were detailed in Table 3.

Example 13

The reaction system for producing aniline by the hydrogenation of nitrobenzene as shown in FIG. 1 was used. The gas replacement apparatus as shown in FIG. 3 was used as the degassing tank for the spent catalyst and the degassing tank for the catalyst to be activated. The degassing tank for the spent catalyst and the degassing tank for the catalyst to be activated were degassed according to the degassing process as shown in FIG. 2.

In the degassing tank for the spent catalyst and the degassing tank for the catalyst to be activated, the ratio of the cross-sectional area of the middle part of the second gas replacement region to the cross-sectional area of the middle part of the first gas replacement region was 15, the number of the flow rectifier(s) contained by any flow disturbance structural member in the first gas replacement region was 4, the number of the flow rectifier(s) contained by any flow disturbance structural member in the second gas replacement region was 20, the flow rectifier was a streamline flow rectifier, the ratio of the cross-sectional area of the run-through flow channel to the maximum cross-sectional area of the corresponding flow rectifier was 10:100, the ratio of the sum of the maximum cross-sectional areas of the multiple flow rectifiers to the corresponding cross-sectional area of the corresponding gas replacement region was 50:100, the number of the flow disturbance structural member(s) disposed in the first gas replacement region was 2, the number of the flow disturbance structural member(s) disposed in the second gas replacement region was 2, the ratio of the vertical distance of any two flow disturbance structural members in relation to one another to (the height of) the corresponding gas replacement region was 0.5, the ratio of the height of the second gas replacement region to the height of the first gas replacement region was 1.5.

The catalyst was a metal loaded catalyst with copper as the main active component, the support was silica, the catalyst had an average particle diameter of 400 μm, and the content of particles lower than 80 μm was 6%. The reaction conditions in the fluidized bed reactor were as follows: the gas superficial velocity was 0.4 m/s, the molar ratio of hydrogen gas to nitrobenzene was 11, the average reaction temperature in the dense phase reaction zone was controlled at 240° C., and the reaction pressure in the dense phase reaction zone was 0.1 MPa. The reaction conditions in the regenerator were as follows: the gas superficial velocity was 0.3 m/s, and the average regeneration temperature was 410° C.; and the reaction conditions in the activator were as follows: the gas superficial velocity was 0.3 m/s, and the average activation temperature was 220° C. The ratio of the superficial velocity of the first gas replacement step to the superficial velocity of the second gas replacement step in the degassing tank for the spent catalyst was 1/5, the degassing agent was nitrogen gas; the ratio of the superficial velocity of the first gas replacement step to the superficial velocity of the second gas replacement step in the degassing tank for the catalyst to be activated was 1/5, the degassing agent was nitrogen gas. In the first gas replacement steps for the degassing tank for the spent catalyst and for the degassing tank for the catalyst to be activated, the average solid content rates were both 0.55; in the second gas replacement steps for the degassing tank for the spent catalyst and for the degassing tank for the catalyst to be activated, the average solid content rates were both 0.12.

The degassing efficiencies for the degassing tank for the spent catalyst and the degassing tank for the catalyst to be activated were both 98.6%, the carbon deposition amount when the reaction time was 90 minutes under the high space velocity condition (0.9 h$^{-1}$) could be controlled at no greater than 0.5%, and the results were detailed in Table 3.

Example 14

The reaction system for producing aniline by the hydrogenation of nitrobenzene as shown in FIG. 1 was used. The gas replacement apparatus as shown in FIG. 3 was used as the degassing tank for the spent catalyst and the degassing tank for the catalyst to be activated. The degassing tank for the spent catalyst and the degassing tank for the catalyst to be activated were degassed according to the degassing process as shown in FIG. 2.

In the degassing tank for the spent catalyst and the degassing tank for the catalyst to be activated, the ratio of the cross-sectional area of the middle part of the second gas replacement region to the cross-sectional area of the middle part of the first gas replacement region was 30, the number of the flow rectifier(s) contained by any flow disturbance structural member in the first gas replacement region was 4, the number of the flow rectifier(s) contained by any flow disturbance structural member in the second gas replacement region was 20, the flow rectifier was a streamline flow rectifier, the ratio of the cross-sectional area of the run-through flow channel to the maximum cross-sectional area of the corresponding flow rectifier was 10:100, the ratio of the sum of the maximum cross-sectional areas of the multiple flow rectifiers to the corresponding cross-sectional area of the corresponding gas replacement region was 50:100, the number of the flow disturbance structural member(s) disposed in the first gas replacement region was 2, the number of the flow disturbance structural member(s) disposed in the second gas replacement region was 2, the ratio of the vertical distance of any two flow disturbance structural members in relation to one another to (the height of) the corresponding gas replacement region was 0.5, the ratio of the height of the second gas replacement region to the height of the first gas replacement region was 1.5.

The catalyst was a metal loaded catalyst with copper as the main active component, the support was silica, the catalyst had an average particle diameter of 400 µm, and the content of particles lower than 80 µm was 6%. The reaction conditions in the fluidized bed reactor were as follows: the gas superficial velocity was 0.4 m/s, the molar ratio of hydrogen gas to nitrobenzene was 11, the average reaction temperature in the dense phase reaction zone was controlled at 240° C., and the reaction pressure in the dense phase reaction zone was 0.1 MPa. The reaction conditions in the regenerator were as follows: the gas superficial velocity was 0.3 m/s, and the average regeneration temperature was 410° C.; and the reaction conditions in the activator were as follows: the gas superficial velocity was 0.3 m/s, and the average activation temperature was 220° C. The ratio of the superficial velocity of the first gas replacement step to the superficial velocity of the second gas replacement step in the degassing tank for the spent catalyst was 1/5, the degassing agent was nitrogen gas; the ratio of the superficial velocity of the first gas replacement step to the superficial velocity of the second gas replacement step in the degassing tank for the catalyst to be activated was 1/5, the degassing agent was nitrogen gas. In the first gas replacement steps for the degassing tank for the spent catalyst and for the degassing tank for the catalyst to be activated, the average solid content rates were both 0.55; in the second gas replacement steps for the degassing tank for the spent catalyst and for the degassing tank for the catalyst to be activated, the average solid content rates were both 0.12.

The degassing efficiencies for the degassing tank for the spent catalyst and the degassing tank for the catalyst to be activated were both 98.6%, the carbon deposition amount when the reaction time was 90 minutes under the high space velocity condition (0.9 $h^{-1}$) could be controlled at no greater than 0.5%, and the results were detailed in Table 3.

Example 15

The reaction system for producing aniline by the hydrogenation of nitrobenzene as shown in FIG. 1 was used. The gas replacement apparatus as shown in FIG. 3 was used as the degassing tank for the spent catalyst and the degassing tank for the catalyst to be activated. The degassing tank for the spent catalyst and the degassing tank for the catalyst to be activated were degassed according to the degassing process as shown in FIG. 2.

In the degassing tank for the spent catalyst and the degassing tank for the catalyst to be activated, the ratio of the cross-sectional area of the middle part of the second gas replacement region to the cross-sectional area of the middle part of the first gas replacement region was 7, the number of the flow rectifier(s) contained by any flow disturbance structural member in the first gas replacement region was 12, the number of the flow rectifier(s) contained by any flow disturbance structural member in the second gas replacement region was 20, the flow rectifier was a streamline flow rectifier, the ratio of the cross-sectional area of the run-through flow channel to the maximum cross-sectional area of the corresponding flow rectifier was 10:100, the ratio of the sum of the maximum cross-sectional areas of the multiple flow rectifiers to the corresponding cross-sectional area of the corresponding gas replacement region was 50:100, the number of the flow disturbance structural member(s) disposed in the first gas replacement region was 2, the number of the flow disturbance structural member(s) disposed in the second gas replacement region was 2, the ratio of the vertical distance of any two flow disturbance structural members in relation to one another to (the height of) the corresponding gas replacement region was 0.5, the ratio of the height of the second gas replacement region to the height of the first gas replacement region was 1.5.

The catalyst was a metal loaded catalyst with copper as the main active component, the support was silica, the catalyst had an average particle diameter of 400 µm, and the content of particles lower than 80 µm was 6%. The reaction conditions in the fluidized bed reactor were as follows: the gas superficial velocity was 0.4 m/s, the molar ratio of hydrogen gas to nitrobenzene was 11, the average reaction temperature in the dense phase reaction zone was controlled at 240° C., and the reaction pressure in the dense phase reaction zone was 0.1 MPa. The reaction conditions in the regenerator were as follows: the gas superficial velocity was 0.3 m/s, and the average regeneration temperature was 410° C.; and the reaction conditions in the activator were as follows: the gas superficial velocity was 0.3 m/s, and the average activation temperature was 220° C. The ratio of the superficial velocity of the first gas replacement step to the superficial velocity of the second gas replacement step in the degassing tank for the spent catalyst was 1/5, the degassing agent was nitrogen gas; the ratio of the superficial velocity of the first gas replacement step to the superficial velocity of the second gas replacement step in the degassing tank for the catalyst to be activated was 1/5, the degassing agent was nitrogen gas. In the first gas replacement steps for the degassing tank for the spent catalyst and for the degassing tank for the catalyst to be activated, the average solid content rates were both 0.55; in the second gas replacement steps for the degassing tank for the spent catalyst and for the degassing tank for the catalyst to be activated, the average solid content rates were both 0.12.

The degassing efficiencies for the degassing tank for the spent catalyst and the degassing tank for the catalyst to be activated were both 99.1%, the carbon deposition amount when the reaction time was 90 minutes under the high space velocity condition (0.9 $h^{-1}$) could be controlled at no greater than 0.5%, and the results were detailed in Table 3.

Example 16

The reaction system for producing aniline by the hydrogenation of nitrobenzene as shown in FIG. 1 was used. The gas replacement apparatus as shown in FIG. 3 was used as the degassing tank for the spent catalyst and the degassing tank for the catalyst to be activated. The degassing tank for the spent catalyst and the degassing tank for the catalyst to be activated were degassed according to the degassing process as shown in FIG. 2.

In the degassing tank for the spent catalyst and the degassing tank for the catalyst to be activated, the ratio of the cross-sectional area of the middle part of the second gas replacement region to the cross-sectional area of the middle part of the first gas replacement region was 7, the number of the flow rectifier(s) contained by any flow disturbance structural member in the first gas replacement region was 4, the number of the flow rectifier(s) contained by any flow disturbance structural member in the second gas replacement region was 36, the flow rectifier was a streamline flow rectifier, the ratio of the cross-sectional area of the run-through flow channel to the maximum cross-sectional area of the corresponding flow rectifier was 10:100, the ratio of the sum of the maximum cross-sectional areas of the multiple flow rectifiers to the corresponding cross-sectional area of the corresponding gas replacement region was 50:100, the number of the flow disturbance structural member(s) disposed in the first gas replacement region was 2, the number of the flow disturbance structural member(s) disposed in the second gas replacement region was 2, the ratio of the vertical distance of any two flow disturbance structural members in relation to one another to (the height of) the corresponding gas replacement region was 0.5, the ratio of the height of the second gas replacement region to the height of the first gas replacement region was 1.5.

The catalyst was a metal loaded catalyst with copper as the main active component, the support was silica, the catalyst had an average particle diameter of 400 μm, and the content of particles lower than 80 μm was 6%. The reaction conditions in the fluidized bed reactor were as follows: the gas superficial velocity was 0.4 m/s, the molar ratio of hydrogen gas to nitrobenzene was 11, the average reaction temperature in the dense phase reaction zone was controlled at 240° C., and the reaction pressure in the dense phase reaction zone was 0.1 MPa. The reaction conditions in the regenerator were as follows: the gas superficial velocity was 0.3 m/s, and the average regeneration temperature was 410° C.; and the reaction conditions in the activator were as follows: the gas superficial velocity was 0.3 m/s, and the average activation temperature was 220° C. The ratio of the superficial velocity of the first gas replacement step to the superficial velocity of the second gas replacement step in the degassing tank for the spent catalyst was 1/5, the degassing agent was nitrogen gas; the ratio of the superficial velocity of the first gas replacement step to the superficial velocity of the second gas replacement step in the degassing tank for the catalyst to be activated was 1/5, the degassing agent was nitrogen gas. In the first gas replacement steps for the degassing tank for the spent catalyst and for the degassing tank for the catalyst to be activated, the average solid content rates were both 0.55; in the second gas replacement steps for the degassing tank for the spent catalyst and for the degassing tank for the catalyst to be activated, the average solid content rates were both 0.12.

The degassing efficiencies for the degassing tank for the spent catalyst and the degassing tank for the catalyst to be activated were both 98.9%, the carbon deposition amount when the reaction time was 90 minutes under the high space velocity condition (0.9 h$^{-1}$) could be controlled at no greater than 0.5%, and the results were detailed in Table 4.

Example 17

The reaction system for producing aniline by the hydrogenation of nitrobenzene as shown in FIG. 1 was used. The gas replacement apparatus as shown in FIG. 3 was used as the degassing tank for the spent catalyst and the degassing tank for the catalyst to be activated. The degassing tank for the spent catalyst and the degassing tank for the catalyst to be activated were degassed according to the degassing process as shown in FIG. 2.

In the degassing tank for the spent catalyst and the degassing tank for the catalyst to be activated, the ratio of the cross-sectional area of the middle part of the second gas replacement region to the cross-sectional area of the middle part of the first gas replacement region was 7, the number of the flow rectifier(s) contained by any flow disturbance structural member in the first gas replacement region was 4, the number of the flow rectifier(s) contained by any flow disturbance structural member in the second gas replacement region was 20, the flow rectifier was a diamond-shaped flow rectifier, the ratio of the cross-sectional area of the run-through flow channel to the maximum cross-sectional area of the corresponding flow rectifier was 10:100, the ratio of the sum of the maximum cross-sectional areas of the multiple flow rectifiers to the corresponding cross-sectional area of the corresponding gas replacement region was 50:100, the number of the flow disturbance structural member(s) disposed in the first gas replacement region was 2, the number of the flow disturbance structural member(s) disposed in the second gas replacement region was 2, the ratio of the vertical distance of any two flow disturbance structural members in relation to one another to (the height of) the corresponding gas replacement region was 0.5, the ratio of the height of the second gas replacement region to the height of the first gas replacement region was 1.5.

The catalyst was a metal loaded catalyst with copper as the main active component, the support was silica, the catalyst had an average particle diameter of 400 μm, and the content of particles lower than 80 μm was 6%. The reaction conditions in the fluidized bed reactor were as follows: the gas superficial velocity was 0.4 m/s, the molar ratio of hydrogen gas to nitrobenzene was 11, the average reaction temperature in the dense phase reaction zone was controlled at 240° C., and the reaction pressure in the dense phase reaction zone was 0.1 MPa. The reaction conditions in the regenerator were as follows: the gas superficial velocity was 0.3 m/s, and the average regeneration temperature was 410° C.; and the reaction conditions in the activator were as follows: the gas superficial velocity was 0.3 m/s, and the average activation temperature was 220° C. The ratio of the superficial velocity of the first gas replacement step to the superficial velocity of the second gas replacement step in the degassing tank for the spent catalyst was 1/5, the degassing agent was nitrogen gas; the ratio of the superficial velocity of the first gas replacement step to the superficial velocity of the second gas replacement step in the degassing tank for the catalyst to be activated was 1/5, the degassing agent was nitrogen gas. In the first gas replacement steps for the degassing tank for the spent catalyst and for the degassing tank for the catalyst to be activated, the average solid content rates were both 0.55; in the second gas replacement steps for the degassing tank for the spent catalyst and for the degassing tank for the catalyst to be activated, the average solid content rates were both 0.12.

The degassing efficiencies for the degassing tank for the spent catalyst and the degassing tank for the catalyst to be activated were both 98.2%, the carbon deposition amount when the reaction time was 90 minutes under the high space velocity condition (0.9 h$^{-1}$) could be controlled at no greater than 0.5%, and the results were detailed in Table 4.

Example 18

The reaction system for producing aniline by the hydrogenation of nitrobenzene as shown in FIG. 1 was used. The gas replacement apparatus as shown in FIG. 3 was used as the degassing tank for the spent catalyst and the degassing tank for the catalyst to be activated. The degassing tank for the spent catalyst and the degassing tank for the catalyst to be activated were degassed according to the degassing process as shown in FIG. 2.

In the degassing tank for the spent catalyst and the degassing tank for the catalyst to be activated, the ratio of the cross-sectional area of the middle part of the second gas replacement region to the cross-sectional area of the middle part of the first gas replacement region was 7, the number of the flow rectifier(s) contained by any flow disturbance structural member in the first gas replacement region was 4, the number of the flow rectifier(s) contained by any flow disturbance structural member in the second gas replacement region was 20, the flow rectifier is an inclined baffle cross-flow type flow rectifier, the ratio of the cross-sectional area of the run-through flow channel to the maximum cross-sectional area of the corresponding flow rectifier was 10:100, the ratio of the sum of the maximum cross-sectional areas of the multiple flow rectifiers to the corresponding cross-sectional area of the corresponding gas replacement region was 50:100, the number of the flow disturbance structural member(s) disposed in the first gas replacement region was 2, the number of the flow disturbance structural member(s) disposed in the second gas replacement region was 2, the ratio of the vertical distance of any two flow disturbance structural members in relation to one another to (the height of) the corresponding gas replacement region was 0.5, the ratio of the height of the second gas replacement region to the height of the first gas replacement region was 1.5.

The catalyst was a metal loaded catalyst with copper as the main active component, the support was silica, the catalyst had an average particle diameter of 400 µm, and the content of particles lower than 80 µm was 6%. The reaction conditions in the fluidized bed reactor were as follows: the gas superficial velocity was 0.4 m/s, the molar ratio of hydrogen gas to nitrobenzene was 11, the average reaction temperature in the dense phase reaction zone was controlled at 240° C., and the reaction pressure in the dense phase reaction zone was 0.1 MPa. The reaction conditions in the regenerator were as follows: the gas superficial velocity was 0.3 m/s, and the average regeneration temperature was 410° C.; and the reaction conditions in the activator were as follows: the gas superficial velocity was 0.3 m/s, and the average activation temperature was 220° C. The ratio of the superficial velocity of the first gas replacement step to the superficial velocity of the second gas replacement step in the degassing tank for the spent catalyst was 1/5, the degassing agent was nitrogen gas; the ratio of the superficial velocity of the first gas replacement step to the superficial velocity of the second gas replacement step in the degassing tank for the catalyst to be activated was 1/5, the degassing agent was nitrogen gas. In the first gas replacement steps for the degassing tank for the spent catalyst and for the degassing tank for the catalyst to be activated, the average solid content rates were both 0.55; in the second gas replacement steps for the degassing tank for the spent catalyst and for the degassing tank for the catalyst to be activated, the average solid content rates were both 0.12.

The degassing efficiencies for the degassing tank for the spent catalyst and the degassing tank for the catalyst to be activated were both 97.9%, the carbon deposition amount when the reaction time was 90 minutes under the high space velocity condition (0.9 h$^{-1}$) could be controlled at no greater than 0.5%, and the results were detailed in Table 4.

Example 19

The reaction system for producing aniline by the hydrogenation of nitrobenzene as shown in FIG. 1 was used. The gas replacement apparatus as shown in FIG. 3 was used as the degassing tank for the spent catalyst and the degassing tank for the catalyst to be activated. The degassing tank for the spent catalyst and the degassing tank for the catalyst to be activated were degassed according to the degassing process as shown in FIG. 2.

In the degassing tank for the spent catalyst and the degassing tank for the catalyst to be activated, the ratio of the cross-sectional area of the middle part of the second gas replacement region to the cross-sectional area of the middle part of the first gas replacement region was 7, the number of the flow rectifier(s) contained by any flow disturbance structural member in the first gas replacement region was 4, the number of the flow rectifier(s) contained by any flow disturbance structural member in the second gas replacement region was 20, the flow rectifier was a flow rectifier-type one, the ratio of the cross-sectional area of the run-through flow channel to the maximum cross-sectional area of the corresponding flow rectifier was 15:100, the ratio of the sum of the maximum cross-sectional areas of the multiple flow rectifiers to the corresponding cross-sectional area of the corresponding gas replacement region was 50:100, the number of the flow disturbance structural member(s) disposed in the first gas replacement region was 2, the number of the flow disturbance structural member(s) disposed in the second gas replacement region was 2, the ratio of the vertical distance of any two flow disturbance structural members in relation to one another to (the height of) the corresponding gas replacement region was 0.5, the ratio of the height of the second gas replacement region to the height of the first gas replacement region was 1.5.

The catalyst was a metal loaded catalyst with copper as the main active component, the support was silica, the catalyst had an average particle diameter of 400 µm, and the content of particles lower than 80 µm was 6%. The reaction conditions in the fluidized bed reactor were as follows: the gas superficial velocity was 0.4 m/s, the molar ratio of hydrogen gas to nitrobenzene was 11, the average reaction temperature in the dense phase reaction zone was controlled at 240° C., and the reaction pressure in the dense phase reaction zone was 0.1 MPa. The reaction conditions in the regenerator were as follows: the gas superficial velocity was 0.3 m/s, and the average regeneration temperature was 410° C.; and the reaction conditions in the activator were as follows: the gas superficial velocity was 0.3 m/s, and the average activation temperature was 220° C. The ratio of the superficial velocity of the first gas replacement step to the superficial velocity of the second gas replacement step in the degassing tank for the spent catalyst was 1/5, the degassing agent was nitrogen gas; the ratio of the superficial velocity of the first gas replacement step to the superficial velocity of the second gas replacement step in the degassing tank for the catalyst to be activated was 1/5, the degassing agent was nitrogen gas. In the first gas replacement steps for the degassing tank for the spent catalyst and for the degassing tank for the catalyst to be activated, the average solid content rates were both 0.55; in the second gas replacement steps for the degassing tank for the spent catalyst and for the degassing tank for the catalyst to be activated, the average solid content rates were both 0.12.

The degassing efficiencies for the degassing tank for the spent catalyst and the degassing tank for the catalyst to be activated were both 97.2%, the carbon deposition amount when the reaction time was 90 minutes under the high space velocity condition (0.9 h$^{-1}$) could be controlled at no greater than 0.5%, and the results were detailed in Table 4.

Example 20

The reaction system for producing aniline by the hydrogenation of nitrobenzene as shown in FIG. 1 was used. The gas replacement apparatus as shown in FIG. 3 was used as the degassing tank for the spent catalyst and the degassing tank for the catalyst to be activated. The degassing tank for the spent catalyst and the degassing tank for the catalyst to be activated were degassed according to the degassing process as shown in FIG. 2.

In the degassing tank for the spent catalyst and the degassing tank for the catalyst to be activated, the ratio of the cross-sectional area of the middle part of the second gas replacement region to the cross-sectional area of the middle part of the first gas replacement region was 7, the number of the flow rectifier(s) contained by any flow disturbance structural member in the first gas replacement region was 4, the number of the flow rectifier(s) contained by any flow disturbance structural member in the second gas replacement region was 20, the flow rectifier was a flow rectifier-type one, the ratio of the cross-sectional area of the run-through flow channel to the maximum cross-sectional area of the corresponding flow rectifier was 3:100, the ratio of the sum of the maximum cross-sectional areas of the multiple flow rectifiers to the corresponding cross-sectional area of the corresponding gas replacement region was 50:100, the number of the flow disturbance structural member(s) disposed in the first gas replacement region was 2, the number of the flow disturbance structural member(s) disposed in the second gas replacement region was 2, the ratio of the vertical distance of any two flow disturbance structural members in relation to one another to (the height of) the corresponding gas replacement region was 0.5, the ratio of the height of the second gas replacement region to the height of the first gas replacement region was 1.5.

The catalyst was a metal loaded catalyst with copper as the main active component, the support was silica, the catalyst had an average particle diameter of 400 μm, and the content of particles lower than 80 μm was 6%. The reaction conditions in the fluidized bed reactor were as follows: the gas superficial velocity was 0.4 m/s, the molar ratio of hydrogen gas to nitrobenzene was 11, the average reaction temperature in the dense phase reaction zone was controlled at 240° C., and the reaction pressure in the dense phase reaction zone was 0.1 MPa. The reaction conditions in the regenerator were as follows: the gas superficial velocity was 0.3 m/s, and the average regeneration temperature was 410° C.; and the reaction conditions in the activator were as follows: the gas superficial velocity was 0.3 m/s, and the average activation temperature was 220° C. The ratio of the superficial velocity of the first gas replacement step to the superficial velocity of the second gas replacement step in the degassing tank for the spent catalyst was 1/5, the degassing agent was nitrogen gas; the ratio of the superficial velocity of the first gas replacement step to the superficial velocity of the second gas replacement step in the degassing tank for the catalyst to be activated was 1/5, the degassing agent was nitrogen gas. In the first gas replacement steps for the degassing tank for the spent catalyst and for the degassing tank for the catalyst to be activated, the average solid content rates were both 0.55; in the second gas replacement steps for the degassing tank for the spent catalyst and for the degassing tank for the catalyst to be activated, the average solid content rates were both 0.12.

The degassing efficiencies for the degassing tank for the spent catalyst and the degassing tank for the catalyst to be activated were both 98.9%, the carbon deposition amount when the reaction time was 90 minutes under the high space velocity condition (0.9 h$^{-1}$) could be controlled at no greater than 0.5%, and the results were detailed in Table 4.

Example 21

The reaction system for producing aniline by the hydrogenation of nitrobenzene as shown in FIG. 1 was used. The gas replacement apparatus as shown in FIG. 3 was used as the degassing tank for the spent catalyst and the degassing tank for the catalyst to be activated. The degassing tank for the spent catalyst and the degassing tank for the catalyst to be activated were degassed according to the degassing process as shown in FIG. 2.

In the degassing tank for the spent catalyst and the degassing tank for the catalyst to be activated, the ratio of the cross-sectional area of the middle part of the second gas replacement region to the cross-sectional area of the middle part of the first gas replacement region was 7, the number of the flow rectifier(s) contained by any flow disturbance structural member in the first gas replacement region was 4, the number of the flow rectifier(s) contained by any flow disturbance structural member in the second gas replacement region was 20, the flow rectifier was a flow rectifier-type one, the ratio of the cross-sectional area of the run-through flow channel to the maximum cross-sectional area of the corresponding flow rectifier was 28:100, the ratio of the sum of the maximum cross-sectional areas of the multiple flow rectifiers to the corresponding cross-sectional area of the corresponding gas replacement region was 50:100, the number of the flow disturbance structural member(s) disposed in the first gas replacement region was 2, the number of the flow disturbance structural member(s) disposed in the second gas replacement region was 2, the ratio of the vertical distance of any two flow disturbance structural members in relation to one another to (the height of) the corresponding gas replacement region was 0.5, the ratio of the height of the second gas replacement region to the height of the first gas replacement region was 1.5.

The catalyst was a metal loaded catalyst with copper as the main active component, the support was silica, the catalyst had an average particle diameter of 400 μm, and the content of particles lower than 80 μm was 6%. The reaction conditions in the fluidized bed reactor were as follows: the gas superficial velocity was 0.4 m/s, the molar ratio of hydrogen gas to nitrobenzene was 11, the average reaction temperature in the dense phase reaction zone was controlled at 240° C., and the reaction pressure in the dense phase reaction zone was 0.1 MPa. The reaction conditions in the regenerator were as follows: the gas superficial velocity was 0.3 m/s, and the average regeneration temperature was 410° C.; and the reaction conditions in the activator were as follows: the gas superficial velocity was 0.3 m/s, and the average activation temperature was 220° C. The ratio of the superficial velocity of the first gas replacement step to the superficial velocity of the second gas replacement step in the degassing tank for the spent catalyst was 1/5, the degassing agent was nitrogen gas; the ratio of the superficial velocity of the first gas replacement step to the superficial velocity of the second gas replacement step in the degassing tank for the catalyst to be activated was 1/5, the degassing agent was nitrogen gas. In the first gas replacement steps for the degassing tank for the spent catalyst and for the degassing tank for the catalyst to be activated, the average solid content rates were both 0.55; in the second gas replacement steps for the degassing tank for the spent catalyst and for the degassing tank for the catalyst to be activated, the average solid content rates were both 0.12.

The degassing efficiencies for the degassing tank for the spent catalyst and the degassing tank for the catalyst to be activated were both 96.8%, the carbon deposition amount when the reaction time was 90 minutes under the high space velocity condition (0.9 h$^{-1}$) could be controlled at no greater than 0.5%, and the results were detailed in Table 5.

Example 22

The reaction system for producing aniline by the hydrogenation of nitrobenzene as shown in FIG. 1 was used. The gas replacement apparatus as shown in FIG. 3 was used as the degassing tank for the spent catalyst and the degassing tank for the catalyst to be activated. The degassing tank for the spent catalyst and the degassing tank for the catalyst to be activated were degassed according to the degassing process as shown in FIG. 2.

In the degassing tank for the spent catalyst and the degassing tank for the catalyst to be activated, the ratio of the cross-sectional area of the middle part of the second gas replacement region to the cross-sectional area of the middle part of the first gas replacement region was 7, the number of the flow rectifier(s) contained by any flow disturbance structural member in the first gas replacement region was 4, the number of the flow rectifier(s) contained by any flow disturbance structural member in the second gas replacement region was 20, the flow rectifier was a flow rectifier-type one, the ratio of the cross-sectional area of the run-through flow channel to the maximum cross-sectional area of the corresponding flow rectifier was 10:100, the ratio of the sum of the maximum cross-sectional areas of the multiple flow rectifiers to the corresponding cross-sectional area of the corresponding gas replacement region was 40:100, the number of the flow disturbance structural member(s) disposed in the first gas replacement region was 2, the number of the flow disturbance structural member(s) disposed in the second gas replacement region was 2, the ratio of the vertical distance of any two flow disturbance structural members in relation to one another to (the height of) the corresponding gas replacement region was 0.5, the ratio of the height of the second gas replacement region to the height of the first gas replacement region was 1.5.

The catalyst was a metal loaded catalyst with copper as the main active component, the support was silica, the catalyst had an average particle diameter of 400 μm, and the content of particles lower than 80 μm was 6%. The reaction conditions in the fluidized bed reactor were as follows: the gas superficial velocity was 0.4 m/s, the molar ratio of hydrogen gas to nitrobenzene was 11, the average reaction temperature in the dense phase reaction zone was controlled at 240° C., and the reaction pressure in the dense phase reaction zone was 0.1 MPa. The reaction conditions in the regenerator were as follows: the gas superficial velocity was 0.3 m/s, and the average regeneration temperature was 410° C.; and the reaction conditions in the activator were as follows: the gas superficial velocity was 0.3 m/s, and the average activation temperature was 220° C. The ratio of the superficial velocity of the first gas replacement step to the superficial velocity of the second gas replacement step in the degassing tank for the spent catalyst was 1/5, the degassing agent was nitrogen gas; the ratio of the superficial velocity of the first gas replacement step to the superficial velocity of the second gas replacement step in the degassing tank for the catalyst to be activated was 1/5, the degassing agent was nitrogen gas. In the first gas replacement steps for the degassing tank for the spent catalyst and for the degassing tank for the catalyst to be activated, the average solid content rates were both 0.55; in the second gas replacement steps for the degassing tank for the spent catalyst and for the degassing tank for the catalyst to be activated, the average solid content rates were both 0.12.

The degassing efficiencies for the degassing tank for the spent catalyst and the degassing tank for the catalyst to be activated were both 98.3%, the carbon deposition amount when the reaction time was 90 minutes under the high space velocity condition ($0.9 \text{ h}^{-1}$) could be controlled at no greater than 0.5%, and the results were detailed in Table 3.

Example 23

The reaction system for producing aniline by the hydrogenation of nitrobenzene as shown in FIG. 1 was used. The gas replacement apparatus as shown in FIG. 3 was used as the degassing tank for the spent catalyst and the degassing tank for the catalyst to be activated. The degassing tank for the spent catalyst and the degassing tank for the catalyst to be activated were degassed according to the degassing process as shown in FIG. 2.

In the degassing tank for the spent catalyst and the degassing tank for the catalyst to be activated, the ratio of the cross-sectional area of the middle part of the second gas replacement region to the cross-sectional area of the middle part of the first gas replacement region was 7, the number of the flow rectifier(s) contained by any flow disturbance structural member in the first gas replacement region was 4, the number of the flow rectifier(s) contained by any flow disturbance structural member in the second gas replacement region was 20, the flow rectifier was a flow rectifier-type one, the ratio of the cross-sectional area of the run-through flow channel to the maximum cross-sectional area of the corresponding flow rectifier was 10:100, the ratio of the sum of the maximum cross-sectional areas of the multiple flow rectifiers to the corresponding cross-sectional area of the corresponding gas replacement region was 65:100, the number of the flow disturbance structural member(s) disposed in the first gas replacement region was 2, the number of the flow disturbance structural member(s) disposed in the second gas replacement region was 2, the ratio of the vertical distance of any two flow disturbance structural members in relation to one another to (the height of) the corresponding gas replacement region was 0.5, the ratio of the height of the second gas replacement region to the height of the first gas replacement region was 1.5.

The catalyst was a metal loaded catalyst with copper as the main active component, the support was silica, the catalyst had an average particle diameter of 400 μm, and the content of particles lower than 80 μm was 6%. The reaction conditions in the fluidized bed reactor were as follows: the gas superficial velocity was 0.4 m/s, the molar ratio of hydrogen gas to nitrobenzene was 11, the average reaction temperature in the dense phase reaction zone was controlled at 240° C., and the reaction pressure in the dense phase reaction zone was 0.1 MPa. The reaction conditions in the regenerator were as follows: the gas superficial velocity was 0.3 m/s, and the average regeneration temperature was 410° C.; and the reaction conditions in the activator were as follows: the gas superficial velocity was 0.3 m/s, and the average activation temperature was 220° C. The ratio of the superficial velocity of the first gas replacement step to the superficial velocity of the second gas replacement step in the degassing tank for the spent catalyst was 1/5, the degassing agent was nitrogen gas; the ratio of the superficial velocity of the first gas replacement step to the superficial velocity of the second gas replacement step in the degassing tank for the catalyst to be activated was 1/5, the degassing agent was nitrogen gas. In the first gas replacement steps for the degassing tank for the spent catalyst and for the degassing tank for the catalyst to be activated, the average solid content rates were both 0.55; in the second gas replacement steps for the degassing tank for the spent catalyst and for the degassing tank for the catalyst to be activated, the average solid content rates were both 0.12.

The degassing efficiencies for the degassing tank for the spent catalyst and the degassing tank for the catalyst to be activated were both 99.0%, the carbon deposition amount when the reaction time was 90 minutes under the high space velocity condition (0.9 h$^{-1}$) could be controlled at no greater than 0.5%, and the results were detailed in Table 5.

Example 24

The reaction system for producing aniline by the hydrogenation of nitrobenzene as shown in FIG. 1 was used. The gas replacement apparatus as shown in FIG. 3 was used as the degassing tank for the spent catalyst and the degassing tank for the catalyst to be activated. The degassing tank for the spent catalyst and the degassing tank for the catalyst to be activated were degassed according to the degassing process as shown in FIG. 2.

In the degassing tank for the spent catalyst and the degassing tank for the catalyst to be activated, the ratio of the cross-sectional area of the middle part of the second gas replacement region to the cross-sectional area of the middle part of the first gas replacement region was 7, the number of the flow rectifier(s) contained by any flow disturbance structural member in the first gas replacement region was 4, the number of the flow rectifier(s) contained by any flow disturbance structural member in the second gas replacement region was 20, the flow rectifier was a flow rectifier-type one, the ratio of the cross-sectional area of the run-through flow channel to the maximum cross-sectional area of the corresponding flow rectifier was 10:100, the ratio of the sum of the maximum cross-sectional areas of the multiple flow rectifiers to the corresponding cross-sectional area of the corresponding gas replacement region was 30:100, the number of the flow disturbance structural member(s) disposed in the first gas replacement region was 2, the number of the flow disturbance structural member(s) disposed in the second gas replacement region was 2, the ratio of the vertical distance of any two flow disturbance structural members in relation to one another to (the height of) the corresponding gas replacement region was 0.5, the ratio of the height of the second gas replacement region to the height of the first gas replacement region was 1.5.

The catalyst was a metal loaded catalyst with copper as the main active component, the support was silica, the catalyst had an average particle diameter of 400 μm, and the content of particles lower than 80 μm was 6%. The reaction conditions in the fluidized bed reactor were as follows: the gas superficial velocity was 0.4 m/s, the molar ratio of hydrogen gas to nitrobenzene was 11, the average reaction temperature in the dense phase reaction zone was controlled at 240° C., and the reaction pressure in the dense phase reaction zone was 0.1 MPa. The reaction conditions in the regenerator were as follows: the gas superficial velocity was 0.3 m/s, and the average regeneration temperature was 410° C.; and the reaction conditions in the activator were as follows: the gas superficial velocity was 0.3 m/s, and the average activation temperature was 220° C. The ratio of the superficial velocity of the first gas replacement step to the superficial velocity of the second gas replacement step in the degassing tank for the spent catalyst was 1/5, the degassing agent was nitrogen gas; the ratio of the superficial velocity of the first gas replacement step to the superficial velocity of the second gas replacement step in the degassing tank for the catalyst to be activated was 1/5, the degassing agent was nitrogen gas. In the first gas replacement steps for the degassing tank for the spent catalyst and for the degassing tank for the catalyst to be activated, the average solid content rates were both 0.55; in the second gas replacement steps for the degassing tank for the spent catalyst and for the degassing tank for the catalyst to be activated, the average solid content rates were both 0.12.

The degassing efficiencies for the degassing tank for the spent catalyst and the degassing tank for the catalyst to be activated were both 97.9%, the carbon deposition amount when the reaction time was 90 minutes under the high space velocity condition (0.9 h$^{-1}$) could be controlled at no greater than 0.5%, and the results were detailed in Table 5.

Example 25

The reaction system for producing aniline by the hydrogenation of nitrobenzene as shown in FIG. 1 was used. The gas replacement apparatus as shown in FIG. 3 was used as the degassing tank for the spent catalyst and the degassing tank for the catalyst to be activated. The degassing tank for the spent catalyst and the degassing tank for the catalyst to be activated were degassed according to the degassing process as shown in FIG. 2.

In the degassing tank for the spent catalyst and the degassing tank for the catalyst to be activated, the ratio of the cross-sectional area of the middle part of the second gas replacement region to the cross-sectional area of the middle part of the first gas replacement region was 7, the number of the flow rectifier(s) contained by any flow disturbance structural member in the first gas replacement region was 4, the number of the flow rectifier(s) contained by any flow disturbance structural member in the second gas replacement region was 20, the flow rectifier was a flow rectifier-type one, the ratio of the cross-sectional area of the run-through flow channel to the maximum cross-sectional area of the corresponding flow rectifier was 10:100, the ratio of the sum of the maximum cross-sectional areas of the multiple flow rectifiers to the corresponding cross-sectional area of the corresponding gas replacement region was 50:100, the number of the flow disturbance structural member(s) disposed in the first gas replacement region was 4, the number of the flow disturbance structural member(s) disposed in the second gas replacement region was 4, the ratio of the vertical distance of any two flow disturbance structural members in relation to one another to (the height of) the corresponding gas replacement region was 0.5, the ratio of the height of the second gas replacement region to the height of the first gas replacement region was 1.5.

The catalyst was a metal loaded catalyst with copper as the main active component, the support was silica, the catalyst had an average particle diameter of 400 μm, and the content of particles lower than 80 μm was 6%. The reaction conditions in the fluidized bed reactor were as follows: the gas superficial velocity was 0.4 m/s, the molar ratio of hydrogen gas to nitrobenzene was 11, the average reaction temperature in the dense phase reaction zone was controlled at 240° C., and the reaction pressure in the dense phase reaction zone was 0.1 MPa. The reaction conditions in the regenerator were as follows: the gas superficial velocity was 0.3 m/s, and the average regeneration temperature was 410° C.; and the reaction conditions in the activator were as follows: the gas superficial velocity was 0.3 m/s, and the average activation temperature was 220° C. The ratio of the superficial velocity of the first gas replacement step to the superficial velocity of the second gas replacement step in the degassing tank for the spent catalyst was 1/5, the degassing agent was nitrogen gas; the ratio of the superficial velocity of the first gas replacement step to the superficial velocity of the second gas replacement step in the degassing tank for the catalyst to be activated was 1/5, the degassing agent was nitrogen gas. In the first gas replacement steps for the degassing tank for the spent catalyst and for the degassing tank for the catalyst to be activated, the average solid content rates were both 0.55; in the second gas replacement steps for the degassing tank for the spent catalyst and for the degassing tank for the catalyst to be activated, the average solid content rates were both 0.12.

The degassing efficiencies for the degassing tank for the spent catalyst and the degassing tank for the catalyst to be activated were both 99.1%, the carbon deposition amount when the reaction time was 90 minutes under the high space velocity condition (0.9 h$^{-1}$) could be controlled at no greater than 0.5%, and the results were detailed in Table 5.

Example 26

The reaction system for producing aniline by the hydrogenation of nitrobenzene as shown in FIG. 1 was used. The gas replacement apparatus as shown in FIG. 3 was used as the degassing tank for the spent catalyst and the degassing tank for the catalyst to be activated. The degassing tank for the spent catalyst and the degassing tank for the catalyst to be activated were degassed according to the degassing process as shown in FIG. 2.

In the degassing tank for the spent catalyst and the degassing tank for the catalyst to be activated, the ratio of the cross-sectional area of the middle part of the second gas replacement region to the cross-sectional area of the middle part of the first gas replacement region was 7, the number of the flow rectifier(s) contained by any flow disturbance structural member in the first gas replacement region was 4, the number of the flow rectifier(s) contained by any flow disturbance structural member in the second gas replacement region was 20, the flow rectifier was a flow rectifier-type one, the ratio of the cross-sectional area of the run-through flow channel to the maximum cross-sectional area of the corresponding flow rectifier was 10:100, the ratio of the sum of the maximum cross-sectional areas of the multiple flow rectifiers to the corresponding cross-sectional area of the corresponding gas replacement region was 50:100, the number of the flow disturbance structural member(s) disposed in the first gas replacement region was 10, the number of the flow disturbance structural member(s) disposed in the second gas replacement region was 10, the ratio of the vertical distance of any two flow disturbance structural members in relation to one another to (the height of) the corresponding gas replacement region was 0.5, the ratio of the height of the second gas replacement region to the height of the first gas replacement region was 1.5.

The catalyst was a metal loaded catalyst with copper as the main active component, the support was silica, the catalyst had an average particle diameter of 400 μm, and the content of particles lower than 80 μm was 6%. The reaction conditions in the fluidized bed reactor were as follows: the gas superficial velocity was 0.4 m/s, the molar ratio of hydrogen gas to nitrobenzene was 11, the average reaction temperature in the dense phase reaction zone was controlled at 240° C., and the reaction pressure in the dense phase reaction zone was 0.1 MPa. The reaction conditions in the regenerator were as follows: the gas superficial velocity was 0.3 m/s, and the average regeneration temperature was 410° C.; and the reaction conditions in the activator were as follows: the gas superficial velocity was 0.3 m/s, and the average activation temperature was 220° C. The ratio of the superficial velocity of the first gas replacement step to the superficial velocity of the second gas replacement step in the degassing tank for the spent catalyst was 1/5, the degassing agent was nitrogen gas; the ratio of the superficial velocity of the first gas replacement step to the superficial velocity of the second gas replacement step in the degassing tank for the catalyst to be activated was 1/5, the degassing agent was nitrogen gas. In the first gas replacement steps for the degassing tank for the spent catalyst and for the degassing tank for the catalyst to be activated, the average solid content rates were both 0.55; in the second gas replacement steps for the degassing tank for the spent catalyst and for the degassing tank for the catalyst to be activated, the average solid content rates were both 0.12.

The degassing efficiencies for the degassing tank for the spent catalyst and the degassing tank for the catalyst to be activated were both 99.2%, the carbon deposition amount when the reaction time was 90 minutes under the high space velocity condition (0.9 h$^{-1}$) could be controlled at no greater than 0.5%, and the results were detailed in Table 6.

Example 27

The reaction system for producing aniline by the hydrogenation of nitrobenzene as shown in FIG. 1 was used. The gas replacement apparatus as shown in FIG. 3 was used as the degassing tank for the spent catalyst and the degassing tank for the catalyst to be activated. The degassing tank for the spent catalyst and the degassing tank for the catalyst to be activated were degassed according to the degassing process as shown in FIG. 2.

In the degassing tank for the spent catalyst and the degassing tank for the catalyst to be activated, the ratio of the cross-sectional area of the middle part of the second gas replacement region to the cross-sectional area of the middle part of the first gas replacement region was 7, the number of the flow rectifier(s) contained by any flow disturbance structural member in the first gas replacement region was 4, the number of the flow rectifier(s) contained by any flow disturbance structural member in the second gas replacement region was 20, the flow rectifier was a flow rectifier-type one, the ratio of the cross-sectional area of the run-through flow channel to the maximum cross-sectional area of the corresponding flow rectifier was 10:100, the ratio of the sum of the maximum cross-sectional areas of the multiple flow rectifiers to the corresponding cross-sectional area of the corresponding gas replacement region was 50:100, the number of the flow disturbance structural member(s) disposed in the first gas replacement region was 2, the number of the flow disturbance structural member(s) disposed in the second gas replacement region was 2, the ratio of the vertical distance of any two flow disturbance structural members in relation to one another to (the height of) the corresponding gas replacement region was 0.02, the ratio of the height of the second gas replacement region to the height of the first gas replacement region was 1.5.

The catalyst was a metal loaded catalyst with copper as the main active component, the support was silica, the catalyst had an average particle diameter of 400 μm, and the content of particles lower than 80 μm was 6%. The reaction conditions in the fluidized bed reactor were as follows: the gas superficial velocity was 0.4 m/s, the molar ratio of hydrogen gas to nitrobenzene was 11, the average reaction temperature in the dense phase reaction zone was controlled at 240° C., and the reaction pressure in the dense phase reaction zone was 0.1 MPa. The reaction conditions in the regenerator were as follows: the gas superficial velocity was 0.3 m/s, and the average regeneration temperature was 410° C.; and the reaction conditions in the activator were as follows: the gas superficial velocity was 0.3 m/s, and the average activation temperature was 220° C. The ratio of the superficial velocity of the first gas replacement step to the superficial velocity of the second gas replacement step in the degassing tank for the spent catalyst was 1/5, the degassing agent was nitrogen gas; the ratio of the superficial velocity of the first gas replacement step to the superficial velocity of the second gas replacement step in the degassing tank for the catalyst to be activated was 1/5, the degassing agent was nitrogen gas. In the first gas replacement steps for the degassing tank for the spent catalyst and for the degassing tank for the catalyst to be activated, the average solid content rates were both 0.55; in the second gas replacement steps for the degassing tank for the spent catalyst and for the degassing tank for the catalyst to be activated, the average solid content rates were both 0.12.

The degassing efficiencies for the degassing tank for the spent catalyst and the degassing tank for the catalyst to be activated were both 99.1%, the carbon deposition amount when the reaction time was 90 minutes under the high space velocity condition (0.9 h$^{-1}$) could be controlled at no greater than 0.5%, and the results were detailed in Table 6.

Example 28

The reaction system for producing aniline by the hydrogenation of nitrobenzene as shown in FIG. 1 was used. The gas replacement apparatus as shown in FIG. 3 was used as the degassing tank for the spent catalyst and the degassing tank for the catalyst to be activated. The degassing tank for the spent catalyst and the degassing tank for the catalyst to be activated were degassed according to the degassing process as shown in FIG. 2.

In the degassing tank for the spent catalyst and the degassing tank for the catalyst to be activated, the ratio of the cross-sectional area of the middle part of the second gas replacement region to the cross-sectional area of the middle part of the first gas replacement region was 7, the number of the flow rectifier(s) contained by any flow disturbance structural member in the first gas replacement region was 4, the number of the flow rectifier(s) contained by any flow disturbance structural member in the second gas replacement region was 20, the flow rectifier was a flow rectifier-type one, the ratio of the cross-sectional area of the run-through flow channel to the maximum cross-sectional area of the corresponding flow rectifier was 10:100, the ratio of the sum of the maximum cross-sectional areas of the multiple flow rectifiers to the corresponding cross-sectional area of the corresponding gas replacement region was 50:100, the number of the flow disturbance structural member(s) disposed in the first gas replacement region was 2, the number of the flow disturbance structural member(s) disposed in the second gas replacement region was 2, the ratio of the vertical distance of any two flow disturbance structural members in relation to one another to (the height of) the corresponding gas replacement region was 0.1, the ratio of the height of the second gas replacement region to the height of the first gas replacement region was 1.5.

The catalyst was a metal loaded catalyst with copper as the main active component, the support was silica, the catalyst had an average particle diameter of 400 μm, and the content of particles lower than 80 μm was 6%. The reaction conditions in the fluidized bed reactor were as follows: the gas superficial velocity was 0.4 m/s, the molar ratio of hydrogen gas to nitrobenzene was 11, the average reaction temperature in the dense phase reaction zone was controlled at 240° C., and the reaction pressure in the dense phase reaction zone was 0.1 MPa. The reaction conditions in the regenerator were as follows: the gas superficial velocity was 0.3 m/s, and the average regeneration temperature was 410° C.; and the reaction conditions in the activator were as follows: the gas superficial velocity was 0.3 m/s, and the average activation temperature was 220° C. The ratio of the superficial velocity of the first gas replacement step to the superficial velocity of the second gas replacement step in the degassing tank for the spent catalyst was 1/5, the degassing agent was nitrogen gas; the ratio of the superficial velocity of the first gas replacement step to the superficial velocity of the second gas replacement step in the degassing tank for the catalyst to be activated was 1/5, the degassing agent was nitrogen gas. In the first gas replacement steps for the degassing tank for the spent catalyst and for the degassing tank for the catalyst to be activated, the average solid content rates were both 0.55; in the second gas replacement steps for the degassing tank for the spent catalyst and for the degassing tank for the catalyst to be activated, the average solid content rates were both 0.12. The degassing efficiencies for the degassing tank for the spent catalyst and the degassing tank for the catalyst to be activated were both 97.6%, the carbon deposition amount when the reaction time was 90 minutes under the high space velocity condition (0.9 h$^{-1}$) could be controlled at no greater than 0.5%, and the results were detailed in Table 6.

Example 29

The reaction system for producing aniline by the hydrogenation of nitrobenzene as shown in FIG. 1 was used. The gas replacement apparatus as shown in FIG. 3 was used as the degassing tank for the spent catalyst and the degassing tank for the catalyst to be activated. The degassing tank for the spent catalyst and the degassing tank for the catalyst to be activated were degassed according to the degassing process as shown in FIG. 2.

In the degassing tank for the spent catalyst and the degassing tank for the catalyst to be activated, the ratio of the cross-sectional area of the middle part of the second gas replacement region to the cross-sectional area of the middle part of the first gas replacement region was 7, the number of the flow rectifier(s) contained by any flow disturbance structural member in the first gas replacement region was 4, the number of the flow rectifier(s) contained by any flow disturbance structural member in the second gas replacement region was 20, the flow rectifier was a flow rectifier-type one, the ratio of the cross-sectional area of the run-through flow channel to the maximum cross-sectional area of the corresponding flow rectifier was 10:100, the ratio of the sum of the maximum cross-sectional areas of the multiple flow rectifiers to the corresponding cross-sectional area of the corresponding gas replacement region was 50:100, the number of the flow disturbance structural member(s) disposed in the first gas replacement region was 2, the number of the flow disturbance structural member(s) disposed in the second gas replacement region was 2, the ratio of the vertical distance of any two flow disturbance structural members in relation to one another to (the height of) the corresponding gas replacement region was 0.5, the ratio of the height of the second gas replacement region to the height of the first gas replacement region was 1.

The catalyst was a metal loaded catalyst with copper as the main active component, the support was silica, the catalyst had an average particle diameter of 400 μm, and the content of particles lower than 80 µm was 6%. The reaction conditions in the fluidized bed reactor were as follows: the gas superficial velocity was 0.4 m/s, the molar ratio of hydrogen gas to nitrobenzene was 11, the average reaction temperature in the dense phase reaction zone was controlled at 240° C., and the reaction pressure in the dense phase reaction zone was 0.1 MPa. The reaction conditions in the regenerator were as follows: the gas superficial velocity was 0.3 m/s, and the average regeneration temperature was 410° C.; and the reaction conditions in the activator were as follows: the gas superficial velocity was 0.3 m/s, and the average activation temperature was 220° C. The ratio of the superficial velocity of the first gas replacement step to the superficial velocity of the second gas replacement step in the degassing tank for the spent catalyst was 1/5, the degassing agent was nitrogen gas; the ratio of the superficial velocity of the first gas replacement step to the superficial velocity of the second gas replacement step in the degassing tank for the catalyst to be activated was 1/5, the degassing agent was nitrogen gas. In the first gas replacement steps for the degassing tank for the spent catalyst and for the degassing tank for the catalyst to be activated, the average solid content rates were both 0.55; in the second gas replacement steps for the degassing tank for the spent catalyst and for the degassing tank for the catalyst to be activated, the average solid content rates were both 0.12.

The degassing efficiencies for the degassing tank for the spent catalyst and the degassing tank for the catalyst to be activated were both 97.6%, the carbon deposition amount when the reaction time was 90 minutes under the high space velocity condition (0.9 h$^{-1}$) could be controlled at no greater than 0.5%, and the results were detailed in Table 6.

Example 30

The reaction system for producing aniline by the hydrogenation of nitrobenzene as shown in FIG. 1 was used. The gas replacement apparatus as shown in FIG. 3 was used as the degassing tank for the spent catalyst and the degassing tank for the catalyst to be activated. The degassing tank for the spent catalyst and the degassing tank for the catalyst to be activated were degassed according to the degassing process as shown in FIG. 2.

In the degassing tank for the spent catalyst and the degassing tank for the catalyst to be activated, the ratio of the cross-sectional area of the middle part of the second gas replacement region to the cross-sectional area of the middle part of the first gas replacement region was 7, the number of the flow rectifier(s) contained by any flow disturbance structural member in the first gas replacement region was 4, the number of the flow rectifier(s) contained by any flow disturbance structural member in the second gas replacement region was 20, the flow rectifier was a flow rectifier-type one, the ratio of the cross-sectional area of the run-through flow channel to the maximum cross-sectional area of the corresponding flow rectifier was 10:100, the ratio of the sum of the maximum cross-sectional areas of the multiple flow rectifiers to the corresponding cross-sectional area of the corresponding gas replacement region was 50:100, the number of the flow disturbance structural member(s) disposed in the first gas replacement region was 2, the number of the flow disturbance structural member(s) disposed in the second gas replacement region was 2, the ratio of the vertical distance of any two flow disturbance structural members in relation to one another to (the height of) the corresponding gas replacement region was 0.5, the ratio of the height of the second gas replacement region to the height of the first gas replacement region was 3.

The catalyst was a metal loaded catalyst with copper as the main active component, the support was silica, the catalyst had an average particle diameter of 400 µm, and the content of particles lower than 80 µm was 6%. The reaction conditions in the fluidized bed reactor were as follows: the gas superficial velocity was 0.4 m/s, the molar ratio of hydrogen gas to nitrobenzene was 11, the average reaction temperature in the dense phase reaction zone was controlled at 240° C., and the reaction pressure in the dense phase reaction zone was 0.1 MPa. The reaction conditions in the regenerator were as follows: the gas superficial velocity was 0.3 m/s, and the average regeneration temperature was 410° C.; and the reaction conditions in the activator were as follows: the gas superficial velocity was 0.3 m/s, and the average activation temperature was 220° C. The ratio of the superficial velocity of the first gas replacement step to the superficial velocity of the second gas replacement step in the degassing tank for the spent catalyst was 1/5, the degassing agent was nitrogen gas; the ratio of the superficial velocity of the first gas replacement step to the superficial velocity of the second gas replacement step in the degassing tank for the catalyst to be activated was 1/5, the degassing agent was nitrogen gas. In the first gas replacement steps for the degassing tank for the spent catalyst and for the degassing tank for the catalyst to be activated, the average solid content rates were both 0.55; in the second gas replacement steps for the degassing tank for the spent catalyst and for the degassing tank for the catalyst to be activated, the average solid content rates were both 0.12.

The degassing efficiencies for the degassing tank for the spent catalyst and the degassing tank for the catalyst to be activated were both 98.9%, the carbon deposition amount when the reaction time was 90 minutes under the high space velocity condition (0.9 h$^{-1}$) could be controlled at no greater than 0.5%, and the results were detailed in Table 6.

Comparative Example 1

The reaction system for producing aniline by the hydrogenation of nitrobenzene as shown in FIG. 1 was used. The degassing tank for the spent catalyst and the degassing tank for the catalyst to be activated were degassed according to the degassing process as shown in FIG. 2. The flow rectifier of the flow disturbance structural member was a streamline flow rectifier.

The catalyst was a metal loaded catalyst with copper as the main active component, the support was silica, the catalyst had an average particle diameter of 400 µm, and the content of particles lower than 80 µm was 6%. The reaction conditions in the fluidized bed reactor were as follows: the gas superficial velocity was 0.4 m/s, the molar ratio of hydrogen gas to nitrobenzene was 11, the average reaction temperature in the dense phase reaction zone was controlled at 240° C., and the reaction pressure in the dense phase reaction zone was 0.1 MPa. The reaction conditions in the regenerator were as follows: the gas superficial velocity was 0.3 m/s, and the average regeneration temperature was 410° C.; and the reaction conditions in the activator were as follows: the gas superficial velocity was 0.3 m/s, and the average activation temperature was 220° C. The ratio of the superficial velocity of the first gas replacement step to the superficial velocity of the second gas replacement step in the degassing tank for the spent catalyst was 1.1, the degassing agent was nitrogen gas; the ratio of the superficial velocity of the first gas replacement step to the superficial velocity of the second gas replacement step in the degassing tank for the catalyst to be activated was 1.1, the degassing agent was nitrogen gas. In the first gas replacement steps for the degassing tank for the spent catalyst and for the degassing tank for the catalyst to be activated, the average solid content rates were both 0.36; in the second gas replacement steps for the degassing tank for the spent catalyst and for the degassing tank for the catalyst to be activated, the average solid content rates were both 0.41.

The degassing efficiencies for the degassing tank for the spent catalyst and the degassing tank for the catalyst to be activated were both 93.1%, the carbon deposition amount when the reaction time was 90 minutes under the high space velocity condition (0.9 $h^{-1}$) could be controlled at no greater than 0.5%, and the results were/are detailed in Table 7.

Comparative Example 2

A prior art reaction system for producing aniline by the hydrogenation of nitrobenzene withnot a regenerator and an activator was used. The used catalyst was a metal loaded catalyst with copper as the main active component, the support was silica, the catalyst had an average particle diameter of 400 μm, and the content of particles lower than 80 μm was 6%, the carbon deposition amount when the reaction time was 90 minutes under the high space velocity condition (0.9 $h^{-1}$) was 3.7%, and the results were detailed in Table 2.

Obviously, the gas replacement apparatus or process of the present invention can solve the problems such as the catalysts prone to coking and deactivation, and the difficulty in the long-period run, and can be used in the industrial run of the nitrobenzene hydrogenation to produce aniline.

TABLE 1

|  | Ex. 1 | Ex. 2 | Ex. 3 | Ex. 4 | Ex. 5 |
| --- | --- | --- | --- | --- | --- |
| Gas superficial veloeity in the regenerator | 0.3 | 0.3 | 0.3 | 0.1 | 0.6 |
| Average regeneration temperature | 410 | 410 | 410 | 410 | 410 |
| Gas superficial veloeity in the activator | 0.3 | 0.3 | 0.3 | 0.3 | 0.3 |
| Average activation temperature | 220 | 220 | 220 | 220 | 220 |
| Ratio of the superficial veloeity of the first gas replacement step to the superficial veloeity of the second gas replacement step in the degassing tank for the spent catalyst | 1/5 | 1/5 | 1/5 | 1/5 | 1/5 |
| Ratio of the superficial veloeity of the regenerated first gas replacement step to the superficial veloeity of the regenerated second gas replacement step | 1/5 | 1/5 | 1/5 | 1/5 | 1/5 |
| Degassing efficiency of the degassing tank for the spent catalyst, % | 98.7 | 97.3 | 97.1 | 98.7 | 98.7 |
| Degassing efficiency of the degassing tank for the catalyst to be activated, % | 98.7 | 97.3 | 97.1 | 98.7 | 98.7 |
| Carbon deposition content when the reaction time was 90 minutes under the high space velocity, % | Could be controlled at no greater than 0.5% | Could be controlled at no greater than 0.5% | Could be controlled at no greater than 0.5% | Could be controlled at no greater than 0.7% | Could be controlled at no greater than 0.3% |

TABLE 2

|  | Ex. 6 | Ex. 7 | Ex. 8 | Ex. 9 | Ex. 10 |
| --- | --- | --- | --- | --- | --- |
| Gas superficial veloeity in the regenerator | 0.3 | 0.3 | 0.3 | 0.3 | 0.3 |
| Average regeneration temperature | 350 | 450 | 410 | 410 | 410 |
| Gas superficial veloeity in the activator | 0.3 | 0.3 | 0.3 | 0.3 | 0.3 |
| Average activation temperature | 220 | 220 | 220 | 220 | 220 |
| Ratio of the superficial veloeity of the first gas replacement step to the superficial veloeity of the second gas replacement step in the degassing tank for the spent catalyst | 1/5 | 1/5 | 1/15 | 1/2 | 1/20 |

TABLE 2-continued

|  | Ex. 6 | Ex. 7 | Ex. 8 | Ex. 9 | Ex. 10 |
| --- | --- | --- | --- | --- | --- |
| Ratio of the superficial velocity of the regenerated first gas replacement step to the superficial velocity of the regenerated second gas replacement step | 1/5 | 1/5 | 1/15 | 1/2 | 1/20 |
| Degassing efficiency of the degassing tank for the spent catalyst, % | 98.7 | 98.7 | 98.2 | 96.8 | 98.9 |
| Degassing efficiency of the degassing tank for the catalyst to be activated, % | 98.7 | 98.7 | 98.2 | 96.8 | 98.9 |
| Carbon deposition content when the reaction time was 90 minutes under the high space velocity, % | Could be controlled at no greater than 1% | Could be controlled at no greater than 0.15% | Could be controlled at no greater than 0.5% | Could be controlled at no greater than 0.5% | Could be controlled at no greater than 0.5% |

TABLE 3

|  | Ex. 11 | Ex. 12 | Ex. 13 | Ex. 14 | Ex. 15 |
| --- | --- | --- | --- | --- | --- |
| Ratio of the cross-sectional area of the middle part of the second gas replacement region to the cross-sectional area of the middle part of the first gas replacement region | 7 | 1.5 | 15 | 30 | 7 |
| Number of the flow rectifier(s) contained by any flow disturbance member in the first gas replacement region | 4 | 4 | 4 | 4 | 12 |
| Number of the flow rectifier(s) contained by any flow disturbance member in the second gas replacement region | 20 | 20 | 20 | 20 | 20 |
| Flow rectifier type | Streamline flow rectifier | Streamline flow rectifier | Streamline flow rectifier | Streamline flow rectifier | Streamline flow rectifier |
| Ratio of the cross-sectional area of the run-through flow channel to the maximum cross-sectional area of the corresponding flow rectifier | 10:100 | 10:100 | 10:100 | 10:100 | 10:100 |
| Ratio of the sum of the maximum cross-sectional areas of the multiple flow rectifiers to the corresponding cross-sectional area of the corresponding gas replacement region | 50:100 | 50:100 | 50:100 | 50:100 | 50:100 |
| Number of the flow disturbance member(s) disposed in the first gas replacement region | 2 | 2 | 2 | 2 | 2 |
| Number of the flow disturbance member(s) disposed in the second gas replacement region | 2 | 2 | 2 | 2 | 2 |
| Ratio of the vertical distance of any two flow disturbance structural members in relation to one another to (the height of) the corresponding gas replacement region | 0.5 | 0.5 | 0.5 | 0.5 | 0.5 |

TABLE 3-continued

|  | Ex. 11 | Ex. 12 | Ex. 13 | Ex. 14 | Ex. 15 |
| --- | --- | --- | --- | --- | --- |
| Ratio of the height of the second gas replacement region to the height of the first gas replacement region | 1.5 | 1.5 | 1.5 | 1.5 | 1.5 |
| Gas superficial velocity in the regenerator | 0.3 | 0.3 | 0.3 | 0.3 | 0.3 |
| Average regeneration temperature | 410 | 410 | 410 | 410 | 410 |
| Gas superficial velocity in the activator | 0.3 | 0.3 | 0.3 | 0.3 | 0.3 |
| Average activation temperature | 220 | 220 | 220 | 220 | 220 |
| Ratio of the superficial velocity of the first gas replacement step to the superficial velocity of the second gas replacement step in the degassing tank for the spent catalyst | 1/5 | 1/5 | 1/5 | 1/5 | 1/5 |
| Ratio of the superficial velocity of the regenerated first gas replacement step to the superficial velocity of the regenerated second gas replacement step | 1/5 | 1/5 | 1/5 | 1/5 | 1/5 |
| Degassing efficiency of the degassing tank for the spent catalyst, % | 98.8 | 96.7 | 98.6 | 98.6 | 99.1 |
| Degassing efficiency of the degassing tank for the catalyst to be activated, % | 98.8 | 96.7 | 98.6 | 98.6 | 99.1 |
| Carbon deposition content when the reaction time was 90 minutes under the high space velocity, % | Could be controlled at no greater than 0.5% | Could be controlled at no greater than 0.5% | Could be controlled at no greater than 0.5% | Could be controlled at no greater than 0.5% | Could be controlled at no greater than 0.5% |

TABLE 4

|  | Ex. 16 | Ex. 17 | Ex. 18 | Ex. 19 | Ex. 20 |
| --- | --- | --- | --- | --- | --- |
| Ratio of the cross-sectional area of the middle part of the second gas replacement region to the cross-sectional area of the middle part of the first gas replacement region | 7 | 7 | 7 | 7 | 7 |
| Number of the flow rectifier(s) contained by any flow disturbance member in the first gas replacement region | 4 | 4 | 4 | 4 | 4 |
| Number of the flow rectifier(s) contained by any flow disturbance member in the second gas replacement region | 36 | 20 | 20 | 20 | 20 |
| Flow rectifier type | Streamline flow rectifier | Diamond-shaped flow rectifier | Inclined baffle cross-flow type flow rectifier | Streamline flow rectifier | Streamline flow rectifier |
| Ratio of the cross-sectional area of the run-through flow channel to the | 10:100 | 10:100 | 10:100 | 15:100 | 3:100 |

TABLE 4-continued

| | Ex. 16 | Ex. 17 | Ex. 18 | Ex. 19 | Ex. 20 |
|---|---|---|---|---|---|
| maximum cross-sectional area of the corresponding flow rectifier | | | | | |
| Ratio of the sum of the maximum cross-sectional areas of the multiple flow rectifiers to the corresponding cross-sectional area of the corresponding gas replacement region | 50:100 | 50:100 | 50:100 | 50:100 | 50:100 |
| Number of the flow disturbance member(s) disposed in the first gas replacement region | 2 | 2 | 2 | 2 | 2 |
| Number of the flow disturbance member(s) disposed in the second gas replacement region | 2 | 2 | 2 | 2 | 2 |
| Ratio of the vertical distance of any two flow disturbance structural members in relation to one another to (the height of) the corresponding gas replacement region | 0.5 | 0.5 | 0.5 | 0.5 | 0.5 |
| Ratio of the height of the second gas replacement region to the height of the first gas replacement region | 1.5 | 1.5 | 1.5 | 1.5 | 1.5 |
| Gas superficial velocity in the regenerator | 0.3 | 0.3 | 0.3 | 0.3 | 0.3 |
| Average regeneration temperature | 410 | 410 | 410 | 410 | 410 |
| Gas superficial velocity in the activator | 0.3 | 0.3 | 0.3 | 0.3 | 0.3 |
| Average activation temperature | 220 | 220 | 220 | 220 | 220 |
| Ratio of the superficial velocity of the first gas replacement step to the superficial velocity of the second gas replacement step in the degassing tank for the spent catalyst | 1/5 | 1/5 | 1/5 | 1/5 | 1/5 |
| Ratio of the superficial velocity of the regenerated first gas replacement step to the superficial velocity of the regenerated second gas replacement step | 1/5 | 1/5 | 1/5 | 1/5 | 1/5 |
| Degassing efficiency of the degassing tank for the spent catalyst, % | 98.9 | 98.2 | 97.9 | 97.2 | 98.9 |
| Degassing efficiency of the degassing tank for the catalyst to be activated, % | 98.9 | 98.2 | 97.9 | 97.2 | 98.9 |
| Carbon deposition content when the reaction time was 90 minutes under the high space velocity, % | Could be controlled at no greater than 0.5% | Could be controlled at no greater than 0.5% | Could be controlled at no greater than 0.5% | Could be controlled at no greater than 0.5% | Could be controlled at no greater than 0.5% |

TABLE 5

|  | Ex. 21 | Ex. 22 | Ex. 23 | Ex. 24 | Ex. 25 |
|---|---|---|---|---|---|
| Ratio of the cross-sectional area of the middle part of the second gas replacement region to the cross-sectional area of the middle part of the first gas replacement region | 7 | 7 | 7 | 7 | 7 |
| Number of the flow rectifier(s) contained by any flow disturbance member in the first gas replacement region | 4 | 4 | 4 | 4 | 4 |
| Number of the flow rectifier(s) contained by any flow disturbance member in the second gas replacement region | 20 | 20 | 20 | 20 | 20 |
| Flow rectifier type | Streamline flow rectifier | Streamline flow rectifier | Streamline flow rectifier | Streamline flow rectifier | Streamline flow rectifier |
| Ratio of the cross-sectional area of the run-through flow channel to the maximum cross-sectional area of the corresponding flow rectifier | 28:100 | 10:100 | 10:100 | 10:100 | 10:100 |
| Ratio of the sum of the maximum cross-sectional areas of the multiple flow rectifiers to the corresponding cross-sectional area of the corresponding gas replacement region | 50:100 | 40:100 | 65:100 | 30:100 | 50:100 |
| Number of the flow disturbance member(s) disposed in the first gas replacement region | 2 | 2 | 2 | 2 | 4 |
| Number of the flow disturbance member(s) disposed in the second gas replacement region | 2 | 2 | 2 | 2 | 4 |
| Ratio of the vertical distance of any two flow disturbance structural members in relation to one another to (the height of) the corresponding gas replacement region | 0.5 | 0.5 | 0.5 | 0.5 | 0.5 |
| Ratio of the height of the second gas replacement region to the height of the first gas replacement region | 1.5 | 1.5 | 1.5 | 1.5 | 1.5 |
| Gas superficial velocity in the regenerator | 0.3 | 0.3 | 0.3 | 0.3 | 0.3 |
| Average regeneration temperature | 410 | 410 | 410 | 410 | 410 |
| Gas superficial velocity in the activator | 0.3 | 0.3 | 0.3 | 0.3 | 0.3 |
| Average activation temperature | 220 | 220 | 220 | 220 | 220 |
| Ratio of the superficial velocity of the first gas replacement step to the superficial velocity of the second gas replacement step in the degassing tank for the spent catalyst | 1/5 | 1/5 | 1/5 | 1/5 | 1/5 |
| Ratio of the superficial velocity of the regenerated first gas | 1/5 | 1/5 | 1/5 | 1/5 | 1/5 |

TABLE 5-continued

|  | Ex. 21 | Ex. 22 | Ex. 23 | Ex. 24 | Ex. 25 |
|---|---|---|---|---|---|
| replacement step to the superficial velocity of the regenerated second gas replacement step |  |  |  |  |  |
| Degassing efficiency of the degassing tank for the spent catalyst, % | 96.8 | 98.3 | 99.0 | 97.9 | 99.1 |
| Degassing efficiency of the degassing tank for the catalyst to be activated, % | 96.8 | 98.3 | 99.0 | 97.9 | 99.1 |
| Carbon deposition content when the reaction time was 90 minutes under the high space velocity, % | Could be controlled at no greater than 0.5% | Could be controlled at no greater than 0.5% | Could be controlled at no greater than 0.5% | Could be controlled at no greater than 0.5% | Could be controlled at no greater than 0.5% |

TABLE 6

|  | Ex. 26 | Ex. 27 | Ex. 28 | Ex. 29 | Ex. 30 |
|---|---|---|---|---|---|
| Ratio of the cross-sectional area of the middle part of the second gas replacement region to the cross-sectional area of the middle part of the first gas replacement region | 7 | 7 | 7 | 7 | 7 |
| Number of the flow rectifier(s) contained by any flow disturbance member in the first gas replacement region | 4 | 4 | 4 | 4 | 4 |
| Number of the flow rectifier(s) contained by any flow disturbance member in the second gas replacement region | 20 | 20 | 20 | 20 | 20 |
| Flow rectifier type | Streamline flow rectifier | Streamline flow rectifier | Streamline flow rectifier | Streamline flow rectifier | Streamline flow rectifier |
| Ratio of the cross-sectional area of the run-through flow channel to the maximum cross-sectional area of the corresponding flow rectifier | 10:100 | 10:100 | 10:100 | 10:100 | 10:100 |
| Ratio of the sum of the maximum cross-sectional areas of the multiple flow rectifiers to the corresponding cross-sectional area of the corresponding gas replacement region | 50:100 | 50:100 | 50:100 | 50:100 | 50:100 |
| Number of the flow disturbance member(s) disposed in the first gas replacement region | 10 | 2 | 2 | 2 | 2 |
| Number of the flow disturbance member(s) disposed in the second gas replacement region | 10 | 2 | 2 | 2 | 2 |
| Ratio of the vertical distance of any two flow disturbance structural members in relation to one another to (the height of) the corresponding gas replacement region | 0.5 | 0.02 | 0.1 | 0.5 | 0.5 |

TABLE 6-continued

|  | Ex. 26 | Ex. 27 | Ex. 28 | Ex. 29 | Ex. 30 |
|---|---|---|---|---|---|
| Ratio of the height of the second gas replacement region to the height of the first gas replacement region | 1.5 | 1.5 | 1.5 | 1 | 3 |
| Gas superficial velocity in the regenerator | 0.3 | 0.3 | 0.3 | 0.3 | 0.3 |
| Average regeneration temperature | 410 | 410 | 410 | 410 | 410 |
| Gas superficial velocity in the activator | 0.3 | 0.3 | 0.3 | 0.3 | 0.3 |
| Average activation temperature | 220 | 220 | 220 | 220 | 220 |
| Ratio of the superficial velocity of the first gas replacement step to the superficial velocity of the second gas replacement step in the degassing tank for the spent catalyst | 1/5 | 1/5 | 1/5 | 1/5 | 1/5 |
| Ratio of the superficial velocity of the regenerated first gas replacement step to the superficial velocity of the regenerated second gas replacement step | 1/5 | 1/5 | 1/5 | 1/5 | 1/5 |
| Degassing efficiency of the degassing tank for the spent catalyst, % | 99.2 | 99.1 | 97.6 | 97.6 | 98.9 |
| Degassing efficiency of the degassing tank for the catalyst to be activated, % | 99.2 | 99.1 | 97.6 | 97.6 | 98.9 |
| Carbon deposition content when the reaction time was 90 minutes under the high space velocity, % | Could be controlled at no greater than 0.5% | Could be controlled at no greater than 0.5% | Could be controlled at no greater than 0.5% | Could be controlled at no greater than 0.5% | Could be controlled at no greater than 0.5% |

TABLE 7

|  | Comparative Example 1 | Comparative Example 2 |
|---|---|---|
| Gas superficial velocity in the regenerator | 0.3 | Using a prior art fluidized bed reactor without a regenerator and an activator |
| Average regeneration temperature | 410 | |
| Gas superficial velocity in the activator | 0.3 | |
| Average activation temperature | 220 | |
| Ratio of the superficial velocity of the first gas replacement step to the superficial velocity of the second gas replacement step in the degassing tank for the spent catalyst | 1.1 | |
| Ratio of the superficial velocity of the regenerated first gas replacement step to the superficial velocity of the regenerated second gas replacement step | 1.1 | |
| Degassing efficiency of the degassing tank for the spent catalyst, % | 93.1 | — |
| Degassing efficiency of the degassing tank for the catalyst to be activated, % | 93.1 | — |
| Carbon deposition content when the reaction time was 90 minutes under the high space velocity, % | Could be controlled at no greater than 0.5% | 3.7 |

The invention claimed is:

1. A degassing process, comprising a first degassing step for degassing a stream to be replaced in the presence of a first replacement gas; and a second degassing step for the degassing in the presence of a second replacement gas, wherein the superficial velocity of the first replacement gas (absolute value, the unit is m/s) is V1, the superficial velocity of the second replacement gas (absolute value, the unit is m/s) is V2, and $100 \geq V2/V1 \geq 2$.

2. The degassing process according to claim 1, wherein the first degassing step has an operating temperature of 0-700° C., and an operating pressure of 0-3 MPaG, and/or, in the first degassing step, the superficial velocity (absolute value) V1 of the first replacement gas is 0.05-0.6 m/s, and the superficial velocity (absolute value) of the stream to be replaced is 0.02-0.2 m/s, and/or, the second degassing step has an operating temperature of 0-700° C., and an operating pressure of 0-3 MPaG, and/or, in the second degassing step, the superficial velocity (absolute value) V2 of the second replacement gas is 0.8-10 m/s, and the superficial velocity (absolute value) of the stream to be replaced is 0.4-6 m/s.

3. The degassing process according to claim 1, wherein in the first degassing step, the gas-solid fluidization characteristics is the bubbling or turbulent fluidization, the solid content is in the range of 0.25-0.6, and/or, in the second degassing step, the gas-solid fluidization characteristics is the turbulent or fast fluidization, the solid content is in the range of 0.02-0.3.

4. The degassing process according to claim 1, wherein the first replacement gas and the stream to be replaced are in countercurrent contact or cocurrent contact, and the second replacement gas and the stream to be replaced are in countercurrent contact or cocurrent contact.

5. The degassing process according to claim 1, wherein the first degassing step and the second degassing step are carried out in different zones of a vessel or carried out separately in different vessels, and/or, the first degassing step and the second degassing step are in the gas-phase communication, and/or, the operating pressure of the first degassing step and the operating pressure of the second degassing step are substantially identical.

6. The degassing process according to claim 1, further comprising one or more degassing steps carried out before the first degassing step, after the first degassing step and before the second degassing step, and/or after the second degassing step.

7. A nitro compound hydrogenation reaction system, comprising at least one fluidized bed reactor and at least one degassing apparatus communicated with said at least one fluidized bed reactor, wherein at least one of the degassing apparatuses is configured to implement the degassing process of claim 1.

8. A nitro compound hydrogenation reaction process, at least comprising a hydrogenation reaction step of contacting a nitro compound as the reaction raw material with hydrogen gas and a hydrogenation catalyst to obtain a reaction product and a spent catalyst; and a degassing step of subjecting the spent catalyst to the degassing in the presence of a replacement gas, wherein the degassing step is proceeded according to the degassing process of claim 1.

9. The hydrogenation reaction process of claim 8, wherein the reaction conditions of the hydrogenation reaction step comprise: the superficial gas velocity is 0.2-0.8 m/s, the molar ratio of hydrogen gas to the reaction raw material is 6-21, the reaction temperature is 220-280° C., the reaction pressure is 0.05-1 MPa (gauge pressure), the hydrogenation catalyst is selected from at least one of a copper-based loaded catalyst, a nickel-based loaded catalyst and a noble metal-based loaded catalyst, and/or, the bulk density of the hydrogenation catalyst is 300-1200 kg/m$^3$, and/or, the average particle diameter of the hydrogenation catalyst is 30-800 μm, and the mass percent of the catalyst particles having a particle diameter of less than 80 μm to the whole catalyst particles is not less than 2 wt %, and/or, the replacement gas is a gas or a vapor, and/or, the nitro compound is selected from at least one of the compounds represented by formula (1),

R—NO$_2$           (1)

in formula (1), R is an optionally substituted C$_{2-20}$ straight, branched or cyclic hydrocarbyl.

10. The process according to claim 1, wherein the stream to be replaced is a liquid stream or solid stream, and/or said first replacement gas is a gas or vapor or steam, and/or said second replacement gas is a gas or vapor or steam, and/or 20≥V2/V1≥2.5.

11. The process according to claim 1, wherein the stream to be replaced is a stream of solid particles, and/or 15≥V2/V1≥5.

12. The process according to claim 2, wherein the first degassing step has an operating temperature of 80-400° C., and an operating pressure of 0.01-1 MPaG, and/or, in the first degassing step, the superficial velocity (absolute value) V1 of the first replacement gas is 0.1-0.3 m/s, and/or the superficial velocity (absolute value) of the stream to be replaced is 0.05-0.1 m/s, and/or, the second degassing step has an operating temperature of 80-400° C., and an operating pressure of 0.01-1 MPaG, and/or, in the second degassing step, the superficial velocity (absolute value) V2 of the second replacement gas is 1-3 m/s, and/or the superficial velocity (absolute value) of the stream to be replaced is 0.6-2.4 m/s.

13. The process according to claim 4, wherein the first replacement gas and the stream to be replaced are in countercurrent contact, and/or the second replacement gas and the stream to be replaced are in cocurrent contact.

14. The reaction system according to claim 7, wherein the at least one fluidized bed reactor comprises catalyst particles, and/or at least one degassing apparatus is disposed downstream of and in communication with said at least one fluidized bed reactor, and/or at least one degassing apparatus is configured to receive an effluent from said at least one fluidized bed reactor, and/or at least one degassing apparatus is configured to receive the spent catalyst particles from said at least one fluidized bed reactor.

15. The hydrogenation reaction process of claim 9, wherein said reaction raw material is nitrobenzene, and/or, the average particle diameter of the hydrogenation catalyst is 40-500 μm, and/or the mass percent of the catalyst particles having a particle diameter of less than 80 μm to the whole catalyst particles is 5-15 wt %, and/or, said replacement gas is selected from at least one of nitrogen gas, water vapor, carbon dioxide, methane, oxygen gas and argon gas, and/or in the structural formula (1), R is an optionally substituted C$_{4-20}$ cyclic hydrocarbyl, or an optionally substituted C$_{6-20}$ aryl, or an optionally substituted phenyl.

* * * * *